United States Patent
Futami et al.

(10) Patent No.: US 9,267,176 B2
(45) Date of Patent: Feb. 23, 2016

(54) METHOD FOR DETECTING NOVEL FGFR4 MUTANT

(75) Inventors: Takashi Futami, Tokyo (JP); Tatsuya Kawase, Tokyo (JP); Nobuaki Shindou, Tokyo (JP); Rumi Takeshita, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 14/236,993

(22) PCT Filed: Aug. 3, 2012

(86) PCT No.: PCT/JP2012/069869
§ 371 (c)(1),
(2), (4) Date: Feb. 4, 2014

(87) PCT Pub. No.: WO2013/021950
PCT Pub. Date: Feb. 14, 2013

(65) Prior Publication Data
US 2014/0220035 A1  Aug. 7, 2014

(30) Foreign Application Priority Data
Aug. 5, 2011 (JP) ................................. 2011-171507

(51) Int. Cl.
*G01N 33/53* (2006.01)
*C12Q 1/68* (2006.01)

(52) U.S. Cl.
CPC ........ *C12Q 1/6886* (2013.01); *C12Q 2600/156* (2013.01)

(58) Field of Classification Search
None
See application file for complete search history.

(56) References Cited

PUBLICATIONS

Database DDBJ/EMBL/GenBank [online], Accession No. NM_002011, http://www.ncbi.nlm.nih.gov/nuccore/47524172?sat=14&satkey=9119313, updated Jul. 16, 2011, retrieved Oct. 17, 2012, Motoda et al., Definition: *Homo sapiens* fibroblast growth factor receptor 4 (FGFR4), transcript variant 1, mRNA, 5 pages.
Database DDBJ/EMBL/GenBank [online], Accession No. NM_022963, http://www.ncbi.nlm.nih.gov/nuccore/47527176?sat=14&satkey=9123497, updated Jul. 16, 2011, retrieved Oct. 17, 2012, Motoda et al., Definition: *Homo sapiens* fibroblast growth factor receptor 4 (FGFR4), transcript variant 2, mRNA., 4 pages.
Database DDBJ/EMBL/GenBank [online], Accession No. NM_213647, http://www.ncbi.nlm.nih.gov/nuccore/47524174?sat=14&satkey=9119426, updated Jul. 16, 2011, retrieved Oct. 17, 2012, Motoda et al., Definition: *Homo sapiens* fibroblast growth factor receptor 4 (FGFR4), transcript variant 3, mRNA, 5 pages.
Roidl et al., "The FGFR4, Y367C mutant is a dominant oncogene in MDA-MB453 breast cancer cells," Oncogene, 2010, 29(10):1543-1552.
Taylor et al., "Identification of FGFR4-activating mutations in human rhabdomyosarcomas that promote metastasis in xenotransplanted models," The Journal of Clinical Investigation, Nov. 2009, 119(11) 3395-3407.
Wesche et al., "Fibroblast growth factors and their receptors in cancer," Biochem. J., 2011 (published online Jun. 28, 2011), 437(2):199-213.
Ye et al., "The Fibroblast Growth Factor Receptor-4 Arg388 Allele is Associated with Gastric Cancer Progression," Ann. Surg. Oncol., 2010, 17(12):3354-3361.
Ezzat et al., "Dual Inhibition of RET and FGFR4 Restrains Medullary Thyroid Cancer Cell Growth," Clinical Cancer Research, Feb. 1, 2005, 11(3):1336-1341.
Roidl et al., "The FGFR4 Y367C mutant is a dominant oncogene in MDA-MB453 breast cancer cells," Oncogene, Nov. 30, 2009, 1-10.

*Primary Examiner* — Michael Pak
(74) *Attorney, Agent, or Firm* — Foley & Lardner LLP

(57) ABSTRACT

[Problem] An object of the present invention is to elucidate a novel genetic mutation which is a cause of cancer, and thereby, to provide a method for detecting the genetic mutation, or a protein which has the mutation, a method for detecting the presence of cancer in a subject, a method for diagnosing cancer in a subject, and a primer set, a probe and a detecting kit for the methods.
[Means for Solution] A method for detecting a fibroblast growth factor receptor 4 (FGFR4) mutant in a subject, which comprises a step of detecting the presence of the mutation of glycine at position 183 in a FGFR4 tyrosine kinase domain to cysteine in a sample obtained from the subject.

5 Claims, No Drawings

METHOD FOR DETECTING NOVEL FGFR4 MUTANT

CROSS-REFERENCE TO RELATED APPLICATIONS

This application is a National Stage application of PCT/JP2012/069869, filed Aug. 3, 2012, which claims priority from Japanese Application No. 2011-171507, filed Aug. 5, 2011.

TECHNICAL FIELD

The present invention relates to a method for detecting a novel mutant of an FGFR4, and a method for detecting cancer using the presence of the mutant as an indicator.

BACKGROUND ART

A fibroblast growth factor receptor (FGFR) is one kind of a receptor tyrosine kinase, and as a ligand of FGFR, a fibroblast growth factor (FGF) has been known. In the FGFR family, the presence of four receptor types, that is, an FGFR1, an FGFR2, an FGFR3 and an FGFR4 has been known. The receptors are made up of a transmembrane protein having an extracellular domain, a transmembrane domain and a cytoplasmic domain. The extracellular domain includes two or three immunoglobulin (Ig) domains. FGFR is a monomeric tyrosine kinase receptor, which is activated by dimerization which occurs on a cell surface in a complex of an FGFR dimer, an FGF, and a heparin glycan or a proteoglycan. For the FGF, 22 kinds of known FGFs are present, and each has an ability to bind to one or a plurality of FGFRs. FGF binds to FGFR, and thereby the receptor tyrosine kinase is activated, and a signal transduction is carried out downstream. Depending on difference in site or period of FGFR expression, complicated biological functions such as a cell migration and a cell proliferation are controlled.

Among the FGFR family, in a FGFR4 gene of human, three human splicing variants (FGFR4 gene variant 1 (GenBank Accession number: NM_002011.3), variant 2 (GenBank Accession number: NM_022963.2) and variant 3 (GenBank Accession number: NM_213647.1)) have been known so far. Among these, the variant 1 and the variant 3 encode an isoform 1 of FGFR4, and the variant 2 encodes an isoform 2 of FGFR4. The FGFR4 isoform 1 is consisting of full length 802 amino acids, and the isoform 2 is consisting of full length 762 amino acids. The isoform 1 and the isoform 2 have a different amino acid sequence in a region in the transmembrane domain, and have the same amino acid sequence in an extracellular domain and a cytoplasmic domain.

It is confirmed that a tyrosine kinase domain of FGFR is present in the cytoplasmic domain, and in various cancers, a point mutation in the tyrosine kinase domain of FGFR is related to activation of cancer. It has been reported that among these, for FGFR4 in rhabdomyoma, an amino acid mutation (N535K, N535D) was found at position 535 in the isoform 1, an introduction of these point mutations causes a constitutive activation of FGFR4, cytoplasmic signals are abnormally activated, and thereby causing canceration and a cell proliferation (Non-Patent Document 1).

However, it has not been reported that an activating point mutation other than the N535K mutation and the N535D mutation is present in the tyrosine kinase domain of FGFR4.

RELATED ART

Non-Patent Document

Non-Patent Document 1: The Journal of Clinical Investigation (United Kingdom), 2009, vol. 11, p. 3395-3407.

DISCLOSURE OF INVENTION

Problems to be Solved by the Invention

An object of the present invention is to elucidate a novel genetic mutation which is a cause of cancer, and thereby, to provide a method for detecting the genetic mutation, or a protein which has the mutation, a method for detecting the presence of cancer in a subject, a method for diagnosing cancer in a subject, a method for identifying a mutation-positive cancer patient, and a primer set, a probe and a detecting kit for the methods.

Means for Solving the Problem

The present invention found that an FGFR4 with a mutation in a tyrosine kinase domain is present in a specimen obtained from a stomach cancer patient (Examples 1 and 2), the mutation in an FGFR4 gene is an activating mutation (Example 5), the infected cells of the mutant FGFR4 gene have a tumorigenicity, and the gene is a responsible gene of cancer (Example 7). Based on these knowledges, the present inventors constructed a method for detecting cancer of the mutant FGFR4 gene, provided a primer set, a probe, and a detecting kit for the method, and enabled to select a cancer patient which becomes subjected to an FGFR4 inhibitor therapy by detecting the mutation FGFR4 gene.

That is, the present invention relates to the following [1] to [15].

[1] A method for detecting a fibroblast growth factor receptor 4 (FGFR4) mutant in a subject, which comprises a step of detecting the presence of a mutation of glycine at position 183 in a FGFR4 tyrosine kinase domain to cysteine in a sample obtained from the subject.

[2] The method described in [1], wherein the mutation is a mutation in a FGFR4 described in the following (1) or (2):
(1) a mutation of glycine at position 636 in FGFR4 isoform 1 to cysteine; or
(2) a mutation of glycine at position 596 in FGFR4 isoform 2 to cysteine.

[3] The method described in [1] or [2], wherein the mutation is a mutation in FGFR4 described in the following (1) or (2):
(1) a mutation of glycine at position 636 in FGFR4 consisting of the amino acid sequence represented by SEQ ID NO: 2 to cysteine; or
(2) a mutation of glycine at position 596 in FGFR4 consisting of the amino acid sequence represented by SEQ ID NO: 4 to cysteine.

[4] The method described in [1] or [2], which comprises a step of detecting the presence of a mutation in FGFR4 gene described in the following (1) or (2):
(1) a mutation of guanine at position 1906 in FGFR4 isoform 1 gene to thymine; or
(2) a mutation of guanine at position 1786 in FGFR4 isoform 2 gene to thymine.

[5] The method described in any one of [1] to [4], which comprises a step of detecting the presence of a mutation in FGFR4 gene described in the following (1) or (2):

(1) a mutation of guanine at position 1906 in FGFR4 gene consisting of the base sequence represented by SEQ ID NO: 1 to thymine; or (2) a mutation of guanine at position 1786 in FGFR4 gene consisting of the base sequence represented by SEQ ID NO: 3 to thymine.

[6] The method described in [2], wherein the mutation is a mutation of glycine at position 636 in FGFR4 isoform 1 to cysteine.

[7] The method described in [6], wherein the mutation is a mutation of glycine at position 636 in FGFR4 consisting of the amino acid sequence represented by SEQ ID NO: 2 to cysteine.

[8] The method described in [6], which comprises a step of detecting the presence of a mutation of guanine at position 1906 in FGFR4 isoform 1 gene to thymine.

[9] The method described in any one of [6] to [8], which comprises a step of detecting the presence of a mutation of guanine at position 1906 in FGFR4 gene consisting of the base sequence represented by SEQ ID NO: 1 to thymine.

[10] The method described in any one of [1] to [9], which comprises a step of amplifying nucleic acids in a sample obtained from the subject by using a primer set which is designed to amplify a region in FGFR4 gene described in the following (1) or (2):

(1) a region comprising a base at position 1906 in FGFR4 gene consisting of the base sequence represented by SEQ ID NO: 1; or (2) a region comprising a base at position 1786 in FGFR4 gene consisting of the base sequence represented by SEQ ID NO: 3.

[11] The method described in [10], wherein the primer set is selected from a group consisting of the following (1) and (2):

(1) a primer set of a sense primer consisting of oligonucleotide of at least any continuous 16 bases between the base number 1 and the base number 1905 of SEQ ID NO: 1 and an antisense primer consisting of oligonucleotide which is complementary to an oligonucleotide of at least any continuous 16 bases between the base number 1907 and the base number 2409 of SEQ ID NO: 1.

(2) a primer set of a sense primer consisting of oligonucleotide of at least any continuous 16 bases between the base number 1 and the base number 1785 of SEQ ID NO: 3 and an antisense primer consisting of oligonucleotide which is complementary to an oligonucleotide of at least any continuous 16 bases between the base number 1787 and the base number 2289 of SEQ ID NO: 3.

[12] The method described in any one of [1] to [9], which comprises a step of hybridizing a probe which is designed to hybridize to a region comprising a mutation in FGFR4 gene described in the following (1) or (2) with nucleic acids in a sample obtained from the subject under stringent condition:

(1) a mutation of guanine at position 1906 in FGFR4 gene consisting of the base sequence represented by SEQ ID NO: 1 to thymine; or (2) a mutation of guanine at position 1786 in FGFR4 gene consisting of the base sequence represented by SEQ ID NO: 3 to thymine.

[13] The method described in any one of [1] to [12], which comprises a step of obtaining a sample from the subject.

[14] The method described in any one of [1] to [13], wherein the subject is a cancer patient.

[15] The method described in [14], wherein the cancer is stomach cancer.

In addition, the present invention relates to the following [16] to [18].

[16] A method for detecting the presence of cancer in a subject, which comprises the step described in any one of [1] to [12].

[17] The method described in [16], which comprises a step of obtaining a sample from the subject.

[18] The method described in [16] or [17], wherein the cancer is stomach cancer.

In addition, the present invention relates to the following [19] to [23].

[19] A method for diagnosing cancer in a subject, which comprises the step described in any one of [1] to [12].

[20] The method described in [19], which comprises a step of obtaining a sample from the subject.

[21] The method described in [19] or [20], which further comprises a step of determining that the subject has a high probability for cancer when the mutation is detected from the sample obtained from the subject.

[22] The method described in [19] or [20], wherein the cancer is stomach cancer.

[23] The method described in [22], which further comprises a step of determining that the subject has a high probability for stomach cancer when the mutation is detected from the sample obtained from the subject.

In addition, the present invention relates to the following [24] to [27].

[24] A method for identifying a subject who is a patient subjected to treatment by a FGFR4 inhibitor, wherein the subject is a cancer patient, which comprises the step described in any one of [1] to [12].

[25] The method described in [24], which comprises a step of obtaining a sample from the subject.

[26] The method described in [24] or [25], which further comprises a step of determining that the subject is a patient subjected to treatment by a FGFR4 inhibitor when the mutation is detected from the sample obtained from the subject.

[27] The method described in any one of [24] to [26], wherein the cancer is stomach cancer.

In addition, the present invention relates to the following [28] to [31].

[28] A primer set for detecting the presence of a mutation of glycine at position 183 in a FGFR4 tyrosine kinase domain to cysteine in a sample obtained from a subject, which is designed to amplify a region in FGFR4 gene described in the following (1) or (2):

(1) a region comprising a base at position 1906 in FGFR4 gene consisting of the base sequence represented by SEQ ID NO: 1; or (2) a region comprising a base at position 1786 in FGFR4 gene consisting of the base sequence represented by SEQ ID NO: 3.

[29] The primer set described in [28], which is selected from a group consisting of the following (1) and (2):

(1) a primer set of a sense primer consisting of oligonucleotide of at least any continuous 16 bases between the base number 1 and the base number 1905 of SEQ ID NO: 1 and an antisense primer consisting of oligonucleotide which is complementary to an oligonucleotide of at least any continuous 16 bases between the base number 1907 and the base number 2409 of SEQ ID NO: 1.

(2) a primer set of a sense primer consisting of oligonucleotide of at least any continuous 16 bases between the base number 1 and the base number 1785 of SEQ ID NO: 3 and an antisense primer consisting of oligonucleotide which is complementary to an oligonucleotide of at least any continuous 16 bases between the base number 1787 and the base number 2289 of SEQ ID NO: 3.

[30] The primer set described in [28] or [29], wherein the subject is cancer patient.

[31] The primer set described in [30], wherein the cancer is stomach cancer.

In addition, the present invention relates to the following [32] to [34].

[32] A probe for detecting the presence of a mutation of glycine at position 183 in a FGFR4 tyrosine kinase domain to cysteine in a sample obtained from a subject, which is designed to hybridize a region comprising a mutation in FGFR4 gene described in the following (1) or (2) under stringent condition:

(1) a mutation of guanine at position 1906 in FGFR4 gene consisting of the base sequence represented by SEQ ID NO: 1 to thymine; or (2) a mutation of guanine at position 1786 in FGFR4 gene consisting of the base sequence represented by SEQ ID NO: 3 to thymine.

[33] The probe described in [32], wherein the subject is cancer patient.

[34] The probe described in [33], wherein the cancer is stomach cancer.

In addition, the present invention relates to the following [35] to [37].

[35] A detecting kit for detecting the presence of a mutation of glycine at position 183 in a FGFR4 tyrosine kinase domain to cysteine in a sample obtained from a subject, which comprises at least one of a primer set described in [28] or [29], or a probe described in [32].

[36] The detecting kit described in [35], wherein the subject is a cancer patient.

[37] The detecting kit described in [36], wherein the cancer is stomach cancer.

In addition, the present invention relates to the following [38] to [45].

[38] A method for detecting the presence of cancer in a subject, which comprises a step of amplifying nucleic acid in a sample obtained from the subject, using the primer set described in [28] or [29].

[39] The method described in [38], which comprises the step of amplifying a region in FGFR4 gene described in the following (1) or (2), using the primer set:

(1) a region comprising a base at position 1906 in FGFR4 isoform 1 gene; or (2) a region comprising a base at position 1786 in FGFR4 isoform 2 gene.

[40] The method described in [38] or [39], which comprises the step of amplifying a region in FGFR4 gene described in the following (1) or (2), using the primer set:

(1) a region comprising a base at position 1906 in FGFR4 gene consisting of the base sequence represented by SEQ ID NO: 1; or (2) a region comprising a base at position 1786 in FGFR4 gene consisting of the base sequence represented by SEQ ID NO: 3.

[41] A method for detecting the presence of cancer in a subject, which comprises the step of hybridizing the probe described in [32] to nucleic acid in a sample obtained from the subject.

[42] The method described in [41], which comprises a step of hybridizing the probe to a region comprising a mutation in FGFR4 gene described in the following (1) or (2):

(1) a mutation of guanine at position 1906 in FGFR4 gene to thymine; or (2) a mutation of guanine at position 1786 in FGFR4 gene to thymine.

[43] The method described in [41] or [42], which comprises a step of hybridizing the probe to a region comprising a mutation in FGFR4 gene described in the following (1) or (2):

(1) a mutation of guanine at position 1906 in FGFR4 gene consisting of the base sequence represented by SEQ ID NO: 1 to thymine; or (2) a mutation of guanine at position 1786 in FGFR4 gene consisting of the base sequence represented by SEQ ID NO: 3 to thymine.

[44] The method described in any one of [38] to [43], which comprises a step of obtaining a sample from the subject.

[45] The method described in any one of [38] to [44], wherein the cancer is stomach cancer.

In addition, the present invention relates to the following [46] to [50].

[46] A method for diagnosing cancer in a subject, which comprises the step described in any one of [38] to [43].

[47] The method described in [46], which comprises a step of obtaining a sample from the subject.

[48] The method described in [46] or [47], which further comprises a step of determining that the subject has a high probability for cancer when the mutation is detected from the sample obtained from the subject.

[49] The method described in [46] or [47], wherein the cancer is stomach cancer.

[50] The method described in [49], which further comprises a step of determining that the subject has a high probability for cancer when the mutation is detected from the sample obtained from the subject.

In addition, the present invention relates to the following [51] to [54].

[51] A method for identifying a subject who is a patient subjected to treatment by a FGFR4 inhibitor, wherein the subject is a cancer patient, which comprises the step described in any one of [38] to [43].

[52] The method described in [51], which comprises a step of obtaining a sample from the subject.

[53] The method described in [51] or [52], which further comprises a step of determining that the subject is a patient subjected to treatment by a FGFR4 inhibitor when the mutation is detected from the sample obtained from the subject.

[54] The method described in any one of [51] to [53], wherein the cancer is stomach cancer.

In addition, the present invention relates to the following [55] to [56].

[55] A method for treating cancer comprising a step of administering a FGFR4 inhibitor to a patient, wherein the patient is identified by any one of the methods [24] to [26] and [51] to [53].

[56] The method described in [55], wherein the subject cancer is stomach cancer.

In addition, the present invention relates to the following [57] to [59].

[57] A FGFR4 mutant polypeptide having a mutation of glycine at position 183 in FGFR4 tyrosine kinase domain to cysteine, or a polypeptide encoding the polypeptide.

[58] A screening method of a cancer therapeutic agent, which comprises a step of evaluating whether a test substance inhibits an activity or an expression of the polynucleotide or polynucleotide or not.

[59] The method described in [58], wherein the cancer is stomach cancer.

Effects of the Invention

The detection method of the present invention is a method for detecting a novel mutant of FGFR4, and can distinguish whether a cancer patient (particularly, a stomach cancer patient) is a subject to which a FGFR4 inhibitor is applied or not. In addition, the method can be used as a method for detecting and diagnosing cancer (particularly, stomach cancer) in a subject. In addition, a primer set, a probe and a detecting kit of the present invention can be used in the method of the present invention.

EMBODIMENTS FOR CARRYING OUT THE INVENTION

Detection Method of the Present Invention

The detection method of the present invention is a method for detecting a fibroblast growth factor receptor 4 (FGFR4) mutant in a subject, which comprises a step of detecting the presence of a mutation of glycine at position 183 in a FGFR4 tyrosine kinase domain to cysteine in a sample obtained from the subject.

As a sample obtained from a subject, materials collected from the subject (sample isolated from a biological body), and specifically, any collected cellular tissues, body fluid (blood, oral mucus, circulating tumor cells, exosomes and the like), and samples obtained from a biopsy are used. The samples obtained from a biopsy are preferably used. Genome DNA or RNA extracted from a collected sample can be used, and the transcription product thereof (product resulting from transcription and translation of a genome; for example, mRNA, cDNA and protein) can also be used. In particular, the prepared mRNA or cDNA are preferably used.

It has been known that two isoforms, that is, isoform 1 and isoform 2 are present in FGFR4. FGFR4 isoform 1 is a FGFR4 consisting of full length 802 amino acids, and for example, a wild-type FGFR4 isoform 1 is consisting of the amino acid sequence represented by SEQ ID NO: 2, and is encoded by polynucleotide consisting of the base sequence represented by SEQ ID NO: 1. FGFR4 isoform 2 is a FGFR4 consisting of amino acids of full length 762 amino acids, and for example, a wild-type FGFR4 isoform 2 is consisting of the amino acid sequence represented by SEQ ID NO: 4, and is encoded by polynucleotide consisting of the base sequence represented by SEQ ID NO: 3. The isoform 1 and the isoform 2 of FGFR4 have a common tyrosine kinase domain in a cytoplasmic region. When used herein, the tyrosine kinase domain of FGFR4 means a region consisting of 311 amino acids which corresponds to amino acids at position 454 to 764 of FGFR4 isoform 1 and amino acids at position 414 to 724 of FGFR4 isoform 2, respectively. The tyrosine kinase domain of the wild-type FGFR4 isoform 1 and isoform 2 is consisting of the amino acid sequence represented by SEQ ID NO: 10, and is encoded by polynucleotide consisting of the base sequence represented by SEQ ID NO: 9.

A mutation which is a detection target in the method of the present invention (referred to as detection target mutation) is a mutation in a tyrosine kinase domain of FGFR4, and specifically, a mutation of glycine at position 183 in a FGFR4 tyrosine kinase domain to cysteine As the representative example of the detection target mutation, a mutation of glycine at position 183 in a FGFR4 tyrosine kinase domain consisting of the amino acid sequence represented by SEQ ID NO: 10 to cysteine is exemplified. The detection target mutation is caused by a mutation in the tyrosine kinase domain coding region of a FGFR4 gene. Therefore, in the method of the present invention, the presence of the gene mutation may be detected. As the representative example of the gene mutation, a mutation of guanine at position 547 in a tyrosine kinase domain coding region of FGFR4 gene consisting of the base sequence represented by SEQ ID NO: 9 to thymine is exemplified.

The above-described detection target mutation corresponds to a mutation of glycine at position 636 in FGFR4 isoform 1 to cysteine, and corresponds to a mutation of glycine at position 596 in FGFR4 isoform 2 to cysteine. In addition, as a mutation in each FGFR4 gene corresponding to these mutations, a mutation of guanine at position 1906 in FGFR4 isoform 1 gene to thymine, and a mutation of guanine at position 1786 in FGFR4 isoform 2 gene to thymine are exemplified.

As more specific examples of the detection target mutation in the method of the present invention, a mutation of glycine at position 636 in FGFR4 consisting of the amino acid sequence represented by SEQ ID NO: 2 to cysteine, and a mutation of glycine at position 596 in FGFR4 consisting of the amino acid sequence represented by SEQ ID NO: 4 to cysteine are exemplified. In addition, as a mutation in each FGFR4 gene corresponding to these, a mutation of guanine at position 1906 in FGFR4 gene consisting of the base sequence represented by SEQ ID NO: 1 to thymine, and a mutation of guanine at position 1786 in FGFR4 gene consisting of the base sequence represented by SEQ ID NO: 3 to thymine are exemplified.

In the method of the present invention, any one of a protein having the detection target mutation (also referred to as a "mutated protein") or a polynucleotide encoding a protein having the detection target mutation (also referred to as a "mutated polynucleotide") may be used as a detection target. As an example of a mutated protein, a protein consisting of the amino acid sequence represented by SEQ ID NO: 6 or SEQ ID NO: 8 is exemplified. In addition, as an example of a mutated polynucleotide, a polynucleotide consisting of the base sequence represented by SEQ ID NO: 5 or SEQ ID NO: 7 is exemplified.

When the presence of a mutated polynucleotide is detected in the detection method of the present invention, the detection step can be performed by detecting the presence of the a mutated polynucleotide in genome DNA of a sample obtained from a subject, or preparing a transcription product (for example, mRNA or cDNA) of genome DNA extracted from a sample obtained from a subject, and detecting the presence of mRNA or cDNA corresponding to a mutated polynucleotide. The extraction of genome DNA, and the preparation of mRNA and cDNA can be performed by a method known in the related art, and can be simply performed using a commercially available kit.

In the detection step, gene mutation analysis methods known in the related art can be used. For example, the detection step comprises a step of amplifying a region comprising a portion corresponding to the detection target mutation (also referred to as a "detection target mutation region") in the mutated polynucleotide using a known nucleic acid amplification method (a PCR method, an RT-PCR method, an LCR method (ligase chain reaction), an SDA method (strand displacement amplification), an NASBA method (nucleic acid sequence-based amplification), an ICAN method (isothermal and chimeric primer-initiated amplification of nucleic acids), an LAMP method (loop-mediated isothermal amplification), a TMA method (gen-probe's TMA system) and the like) with respect to nucleic acid derived from a sample obtained from a subject (for example, mRNA or cDNA), and after the amplification, the presence or absence of the mutation can be confirmed by sequencing of the amplified product. As a sequencing method, a method known in the related art such as a direct sequencing or the like can be used.

A primer used in the nucleic acid amplification method is not particularly limited as long as the detection target mutation region in the mutated polynucleotide can be amplified, and is designed on the basis of the base sequence of the mutated polynucleotide. In designing a primer, softwares for primer designing (for example, primer Express; PE Biosystems) or the like can be used. In addition, since if the size of amplified is huge, amplification efficiency is reduced, the sense primer and the antisense primer are appropriately set such that the size of the amplified product when amplifying mRNA or cDNA as a target is 1 kb or less.

As other known gene mutation analysis method using a nucleic acid amplification method, methods on the basis of PCR such as an RFLP method (restriction fragment length polymorphism analysis method), a TaqMan method, an allele-specific primer PCR (ASP-PCR) method and an SSCP method can also be used. In the RFLP method, if change occurs in a restriction enzyme recognition site on the basis of the mutation, after amplifying the detection target mutation region by PCR, the difference of nucleic acid fragments after the restriction enzyme treatment is analyzed by an electrophoresis. The TaqMan method is a method of adding a probe (TaqMan probe) in which 5' terminal is modified with a fluorescent substance (FAM, VIC and the like), and 3' terminal is modified with a quencher (quenching substance) to PCR reaction system. In this method, when the TaqMan probe is hybridized to the detection target mutation region, and a PCR reaction from a primer is performed, the TaqMan probe is decomposed by the 5'→3' exonuclease activity of DNA polymerase in an extension reaction. By this, fluorescent substance is liberated from the probe, suppression by the quencher is removed, and thus fluorescence from the fluorescent substance is emitted, whereby the mutation of interest is detected. In the ASP-PCR method, a primer is designed so as to have the detection target mutation site at 3' terminal, and the presence or absence of nucleic acid amplification is detected by PCR. In the SSCP method, after the detection target mutation region is PCR-amplified, it is separated into single-strand DNA, and then it is separated by the electrophoresis in a non-denatured gel. A high-dimensional structure of DNA is changed by the mutation, which reflects the difference of mobility on the gel.

In addition, as other known gene mutation analysis method, a method based on a probe hybridization can also be used, and for example, a DNA chip method, an invader method, a melting curve analysis method and the like are exemplified. In the DNA chip method, DNA comprising the detection target mutation region is disposed on a substrate, nucleic acid derived from a subject is hybridized to the DNA chip, and the presence or absence of hybridization is confirmed. In the invader method, after two kinds of nucleic acid (invader oligo and signal probe) that hybridize before and after the detection target mutation site are reacted with nucleic acid derived from a subject, Clevase enzyme which recognizes a triple chain structure of DNA formed is acted, whereby a Flap in the signal probe is liberated. Then, the Flap is hybridized with an FRET probe for detection, and the same enzyme is acted again thereto, whereby fluorescence of the fluorescent substance liberated from the FRET probe is detected. In the melting curve analysis method, after fluorescent labeling probe is hybridized to the detection target mutation region, temperature is gradually increased, and the change of fluorescence by the temperature increase is measured to create a melting curve. Thus, the change in the melting temperature due to the presence or absence of a mutation is confirmed.

In addition, as other known gene mutation analysis method, a method based on primer extension can also be used, and for example, a SNaPshot method and a pyrosequencing method are exemplified. In the SNaPshot method, using the primer adjacent to the detection target mutation site and a ddNTP labeled with a fluorescent label to extend only one base from the primer, the base which is incorporated is detected. In the pyrosequencing method, each dNTP is added in a primer extension reaction, and dNTP is incorporated by the reaction of the polymerase, whereby pyrophosphate is generated. The generated pyrophosphate is detected by a fluorescence reaction by luciferase, and the base sequence is determined from an emission peak pattern.

It is possible for those skilled in the related art to appropriately design the primers and the probes to be used on the basis of the gene mutation analysis method to be used, and without being particularly limited, for example, these may be prepared by a chemical synthesis.

In the detection method of the present invention, the presence of the mutated protein in a sample obtained from a subject may be detected, and for example, it can be performed using an antibody which specifically recognizes the mutated protein. Preparation of such an antibody and detection of protein using the antibody can be performed using methods known in the related art.

In the method of the present invention, it can be determined that a subject has a high probability for cancer (particularly, stomach cancer) when the detection target mutation is detected from a sample obtained from the subject.

In addition, the detection step in the method of the present invention can be used in the detection method of the presence of cancer (particularly, stomach cancer) in a subject, or in a diagnosis method of cancer in a subject. In addition to the detection step, the diagnosis method of the invention may further comprise a step of determining that a subject has a high probability for cancer (particularly, stomach cancer) when the mutation is detected from a sample obtained from the subject. In addition, the detection step can also be used in a method for identifying a subject (a patient with cancer such as a stomach cancer) to which treatment by a FGFR4 inhibitor is applied. In addition to the detection step, the identification method of the invention may further comprise a step of determining that a subject is a patient subjected to treatment by a FGFR4 inhibitor when the mutation is detected from a sample obtained from the subject.

<<Primer Set, Probe and Detecting Kit of the Present Invention>>

The primer set of the present invention is a primer set for detecting the presence of a mutation of glycine at position 183 in a FGFR4 tyrosine kinase domain to cysteine in a sample obtained from the subject, which comprises a sense primer and an antisense primer designed to amplify a detection target mutation region in a mutated polynucleotide in the detection step of the present invention. The antisense primer is consisting of nucleic acid molecule (preferably, nucleic acid molecule of at least 16 bases) hybridizing under stringent condition (preferably, under more stringent condition) to the mutated polynucleotide, and the sense primer is consisting of nucleic acid molecule (preferably, nucleic acid molecule of at least 16 bases) hybridizing under stringent condition (preferably, under more stringent condition) to a complementary strand of the mutated polynucleotide.

Preferably, the primer set of the present invention comprises a sense primer and an antisense primer designed to amplify a region comprising a base at position 1906 in FGFR4 gene consisting of the base sequence represented by SEQ ID NO: 1, and a region comprising a base at position 1786 in FGFR4 gene consisting of the base sequence represented by SEQ ID NO: 3.

As specific aspects of the primer set of the present invention, primer sets selected from a group consisting of the following (1) and (2) are exemplified:
(1) a primer set of a sense primer consisting of oligonucleotide of at least any continuous 16 bases between the base number 1 and the base number 1905 of SEQ ID NO: 1 and an antisense primer consisting of oligonucleotide which is complementary to an oligonucleotide of at least any continuous 16 bases between the base number 1907 and a base number 2409 of SEQ ID NO: 1; and
(2) a primer set of a sense primer consisting of oligonucleotide of at least any continuous 16 bases between the base number 1 and the base number 1785 of SEQ ID NO: 3 and an antisense primer consisting of oligonucleotide which is complementary to an oligonucleotide of at least any continuous 16 bases between the base number 1787 and the base number 2289 of SEQ ID NO: 3.

More preferably, the primer set of the present invention comprises a sense primer and an antisense primer designed to amplify a region comprising the base at position 547 in a tyrosine kinase domain coding region of FGFR4 gene consisting of the base sequence represented by SEQ ID NO: 9, and as specific aspects, primer sets shown below are exemplified.

A primer set of a sense primer consisting of oligonucleotide of at least any continuous 16 bases between the base number 1 and a base number 546 of SEQ ID NO: 9, and an antisense primer consisting of oligonucleotide which is complementary to an oligonucleotide of at least any continuous 16 bases between a base number 548 and a base number 933 of SEQ ID NO: 9.

The primer set of the present invention can be used in the method of the present invention, and for example, a step of amplifying nucleic acid in a sample obtained from a subject using the primer set of the present invention may be included in the method of the present invention.

The probe of the present invention is a probe for detecting the presence of a mutation of glycine at position 183 in a FGFR4 tyrosine kinase domain to cysteine in a sample obtained from the subject, which is designed to hybridize to the detection target mutation region in the mutated polynucleotide in the detection step of the present invention. The probe of the present invention is consisting of nucleic acid molecule (preferably, nucleic acid molecule of at least 16 bases) hybridizing under stringent condition (preferably, under more stringent condition) to the detection target mutation region of the mutated polynucleotide or complementary strand thereof.

Preferably, the probe of the present invention is designed to hybridize to a region comprising a mutation of guanine at position 1906 in FGFR4 gene consisting of the base sequence represented by SEQ ID NO: 1 to thymine, and a mutation of guanine at position 1786 in FGFR4 gene consisting of the base sequence represented by SEQ ID NO: 3 to thymine.

The probe of the present invention can be used in the method of the present invention, and for example, a step of hybridizing the probe of the present invention to nucleic acid in a sample obtained from a subject may be included in the method of the present invention.

The "stringent condition" means "5×SSPE, 5×Denhardt's solution, 0.5% of SDS, 50% of formamide, 200 µg/mL of salmon sperm DNA and overnight at 42° C." as a condition for hybridizing, and "0.5×SSC, 0.1% of SDS and 42° C." as a condition for washing. The "more stringent condition" means "5×SSPE, 5×Denhardt's solution, 0.5% of SDS, 50% of formamide, 200 µg/mL of salmon sperm DNA and overnight at 42° C." as a condition for hybridizing, and "0.2×SSC, 0.1% of SDS and 65° C." as a condition for washing.

In the primer set, it is preferable that a distance between the selected positions of the sense primer and the antisense primer be 1 kb or less, or the size of the amplified product amplified by the sense primer and the antisense primer be 1 kb or less. In addition, the primer and the probe of the present invention normally have a chain length of 15 to 40 bases, preferably 16 to 24 bases, more preferably 18 to 24 bases, and particularly preferably 20 to 24 bases.

For example, the primer and the probe of the present invention can be easily prepared by those skilled in the related art by a chemical synthesis method, and may be labeled with a fluorescent label or the like depending on the detection method.

The detecting kit of the present invention is a kit for detecting the presence of a mutation of glycine at position 183 in a FGFR4 tyrosine kinase domain to cysteine in a sample obtained from the subject, which comprises at least one of the primer set of the present invention or the probe of the present invention. The primer set, the probe and the detecting kit of the present invention can also be used in the method of the present invention described above. For example, the method of the present invention may also comprise a step of amplifying the detection target mutation region using the primer set of the present invention, and may comprise a step of hybridizing the probe of the present invention to the detection target mutation region.

<<Treatment Method of the Present Invention>>

The treatment method of the present invention is a method for treating cancer comprising a step of administering a FGFR4 inhibitor to a cancer (particularly, stomach cancer) patient which is positive for FGFR4 mutation of the present invention. In the treatment method of the present invention, a patient who is identified to be a subject to which treatment by a FGFR4 inhibitor is applied, using the above-described method, can be treated. As a FGFR4 inhibitor, various FGFR4 inhibitors known to those skilled in the related art such as PD173074 (for example, Clin Cancer Res. 2005 Feb. 1; 11 (3):1336-41) and an anti-FGFR4 antibody (for example, MAbs. 2011; 3 (4): 376-86) can be used.

<<Screening Method of the Present Invention>>

The presence of FGFR4 mutant identified by the inventors was detected in a stomach cancer patient, and it was also confirmed that FGFR4 mutant is a responsible gene of cancer. Accordingly, a method of screening substance which inhibits an activity or an expression of FGFR4 mutant of the present invention can be used as a method of screening therapeutic agent of cancer (preferably, stomach cancer) which is positive for FGFR4 mutant of the present invention.

For example, the screening method of the present invention can be performed by contacting a test substance with FGFR4 mutant of the present invention and analyzing whether the activity thereof is inhibited or not, or by contacting a test substance with cells expressing FGFR4 mutant of the present invention and analyzing whether the activity or the expression thereof is inhibited or not. Whether the activity (that is, autophosphorylation activity) of FGFR4 mutant of the present invention is inhibited or not can be determined by analyzing changes in the tyrosine phosphorylation level of FGFR4 mutant of the present invention with which the test substance is contacted, and this can be performed using the assay methods known in the related art. In addition, whether the expression of FGFR4 mutant of the present invention is inhibited or not can be determined by analyzing whether the expression of mRNA or protein in the cells expressing FGFR4 mutant of the present invention with which the test substance is contacted is suppressed or not, and this can be performed using the methods known in the related art such as a quantitative PCR method, an ELISA method or the like. Alternatively, as in Examples described below, an inhibitory activity with respect to a tumor proliferation may be confirmed when cells expressing FGFR4 mutant of the present invention is inoculated to a nude mouse, and a test substance is administered into the mouse.

EXAMPLES

Hereinafter, the present invention will be described in more detail with examples, however, the present invention is not limited to the examples. Moreover, unless otherwise specified, it can be performed according to known methods in the related art. In addition, in the case of using the commercially available reagents and kit, the present invention can follow the instructions from the commercially available products.

Example 1

Discovery of G636C Mutated FGFR4 (G636C-FGFR4) Polynucleotide in a Stomach Cancer Clinical Specimen A reverse transcription reaction was performed with respect to St041 specimen RNA (Asterand in U.S.), which is RNA derived from a stomach cancer patient tissue, using a reverse transcriptase (SuperScript III, Life Technologies Corp.) and an oligo (dT) primer (oligo (dT) 20 primer, Life Technologies Corp.) according to the protocol of the kit, whereby cDNA was synthesized.

Then, PCR (35 cycles of 98° C. for 30 seconds, 52° C. for 30 seconds and 68° C. for 30 seconds was repeated) was performed using primers of SEQ ID NO: 11 and SEQ ID NO: 12, the above-obtained cDNA as a template and DNA polymerase (KOD-Plus-Ver. 2, Toyobo Co., Ltd.). Thereafter, the above-described PCR product was purified using a column (PCR Purification Kit, QIAGEN). Thereafter, a sequence reaction was performed (Big Dye Terminator v3.1 Cycle Sequencing Kit, Life Technologies Corp.) using a primer of SEQ ID NO: 13 and the purified PCR product as a template.

As a result, substitution to thymine (T) from guanine (G) was found at position 1906 in coding region of FGFR4 isoform 1 (GenBank accession number: NM_002011.3 and GenBank accession number: NM_213647.1) (SEQ ID NO: 1) and at position 1786 in coding region of FGFR4 isoform 2 (GenBank accession number: NM_022963.2) (SEQ ID NO: 3), respectively. The mutation is equivalent to a mutation to cysteine (C) from glycine (G) at an amino acid corresponding to position 636 in the amino acid sequence of the isoform 1 (SEQ ID NO: 2), and corresponding to position 596 in the amino acid sequence of the isoform 2 (SEQ ID NO: 4), respectively. FGFR4 mutant having the mutation is also referred to as a G636C-FGFR4.

Example 2

Detection of G636C-FGFR4 in Stomach Cancer Sample

The presence or absence of a G636C-FGFR4 mutation was confirmed with respect to 83 samples of RNA derived from a stomach cancer patient tissue (Asterand in U.S.) using the same method as in Example 1.

As a result, the above-described G636C-FGFR4 mutation was detected in the sample St041. In view of the above, it is possible to detect the presence of G636C-FGFR4 in a sample derived from a stomach cancer clinical specimen, and select a patient positive for G636C-FGFR4 by the above-described method.

Example 3

Cloning of Wild-Type and Mutant FGFR4s

In order to express the full length ORF of G636C-FGFR4 as a protein, first, a wild-type FGFR4 (isoform 1) was cloned. The PCR (30 cycles of 98° C. for 10 seconds, 55° C. for 15 seconds and 68° C. for 2 minutes was repeated 30 times) was performed using primers of SEQ ID NO: 14 (SpeI is included as a restriction enzyme site) and SEQ ID NO: 15 (XhoI is included as a restriction enzyme site), the full length FGFR4 (Ultimate™ ORFCard for Clone ID IOH13371, Life Technologies Corp.) as a template, and DNA polymerase (PrimeSTAR GXL DNA Polymerase, Takara Bio Inc.). The PCR product was cloned into the cloning vector (TOPO XL PCR Cloning Kit, Life Technologies Corp.) (FGFR4/TOPO XL).

Then, using FGFR4/TOPO XL as a template, and primers of SEQ ID NO: 16 and SEQ ID NO: 17, G636C mutation was introduced by a Mutagenesis method (PrimeSTAR (registered trademark) Mutagenesis Basal Kit, Takara Bio Inc.) (G636C-FGFR4/TOPO XL). The base sequence and the amino acid sequence of the prepared G636C-FGFR4 are shown in SEQ ID NO: 5 and SEQ ID NO: 6, respectively.

Example 4

Preparation of Expression Vector of Wild-Type and Mutant FGFR4s

The PCR (30 cycles of 98° C. for 10 seconds, 55° C. for 15 seconds and 68° C. for 2 minutes) was performed using FGFR4/TOPO XL and G636C-FGFR4/TOPO XL as templates, primers of SEQ ID NO: 18 and SEQ ID NO: 19, and DNA polymerase (PrimeSTAR GXL DNA Polymerase, Takara Bio Inc.). After the amplified DNA fragments were subjected to the electrophoresis, they were excised from the gel and subjected to column purification. These PCR fragments were cloned into the pTracer™-CMV Bsd (Life Technologies Corp.) digested by EcoRV using an In-Fusion cloning system (In-Fusion (registered trademark) Advantage PCR Cloning Kit w/Cloning Enhancer, Takara Bio Inc.). Vectors prepared for wild-type and mutant FGFR4 are referred to as FGFR4/pTracer-CMV-Bsd and G636C-FGFR4/pTracer-CMV-Bsd.

Example 5

Confirmation that G636C Mutation is an Activating Mutation

After HEK293 cells were seeded by $2 \times 10^5$ cells in 24 well plate, using transfection reagent (Lipofectamine 2000, Life Technologies Corp.), 400 ng of FGFR4/pTracer-CMV-Bsd or G636C-FGFR4/pTracer-CMV-Bsd was transfected thereto, respectively. The next day, the cells were dissolved in SDS sample buffer, and were subjected to Western blotting. As a result of detection by the anti-phosphorylated FGFR4 antibody (Cell Signaling Technology, Inc) and an anti-phosphorylated ERK1/2 antibody (Cell Signaling Technology, Inc), enhancement of autophosphorylation of FGFR4 and enhancement of phosphorylation of ERK in HEK293 cells into which G636C-FGFR4/pTracer-CMV-Bsd was introduced was observed, compared to FGFR4/pTracer-CMV-Bsd. In view of the above, it was found that the G636C mutation is an activating mutation.

Example 6

Preparation of Lentivirus Expression Vector of Wild-Type and Mutant FGFR4s

FGFR4/TOPO XL was digested with SpeI and XhoI, nucleic acid fragments was cloned into the SpeI-SalI site present in the multiple cloning site of a lentiviral expression vector (pLenti6.3/V5-TOPO, Life Technologies Corp.) which was digested by SpeI and SalI (named as FGFR4/pLenti6.3). In the same manner, the lentivirus expression vector G636C-FGFR4/pLenti6.3 was constructed from G636C-FGFR4/TOPO XL.

Together with 9 µg of plasmid for packaging (ViraPower™ Packaging Mix, Life Technologies Corp.), 3 µg of the above-described FGFR4/pLenti6.3 or G636C-FGFR4/pLenti6.3 was introduced into 293FT cells packaging cell (Life Technologies Corp.) using transfection reagent (Lipofectamine 2000, Life Technologies Corp.). The culture supernatant 3 days after introduction was collected as a lentivirus, polybrene (Sigma-Aldrich Co. LLC.) was added thereto at a concentration of 6 µg/ml, and the resultant was added to mouse NIH3T3 cells. After two days, the culture supernatant of the NIH3T3 cells was replaced with DMEM medium (Invitrogen Corp.) to which 10% bovine serum (Invitrogen Corp.) and 5 µg/ml of Blastcidin (InvivoGen) were added, and further cultured for 2 weeks, thereby obtaining two strains each of NIH3T3 cells stably expressing wild-type FGFR4 and G636C-FGFR4, respectively (named as FGFR4/NIH3T3-e7 and FGFR4/NIH3T3-f7, and G636C-FGFR4/NIH3T3-c1 and G636C-FGFR4/NIH3T3-c2, respectively).

Example 7

Study of Tumorigenicity of G636C-FGFR4

The cell strain was transplanted into a nude mouse to study a tumor forming ability in vivo, and tumorigenicity was studied. Each cell of FGFR4/NIH3T3-e7, FGFR4/NIH3T3-f7, G636C-FGFR4/NIH3T3-c1, and G636C-FGFR4/NIH3T3-c2 is inoculated under the skin of a nude mouse by $3 \times 10^6$ cells, and observation was performed for 22 days. As a result, in the mouse into which FGFR4/NIH3T3-e7 or FGFR4/NIH3T3-f7 was transplanted, tumor formation was not observed. On the other hand, in the mouse into which G636C-FGFR4/NIH3T3-c1 or G636C-FGFR4/NIH3T3-c2 was transplanted, tumor formation was observed. In view of the above, it was found that the G636C-FGFR4 is a responsible gene of cancer.

INDUSTRIAL APPLICABILITY

The detection method of the present invention is a method for detecting a novel mutant of FGFR4, and it is useful for distinguish whether a cancer patient (particularly, a stomach cancer patient) is a subject to which a FGFR4 inhibitor is applied or not. In addition, the method is useful for detecting and diagnosing cancer (particularly, stomach cancer) in a subject. In addition, a primer set, a probe and a detecting kit of the present invention can be used in the method of the present invention.

The invention claimed is:

1. A method for detecting a fibroblast growth factor receptor 4 (FGFR4) mutant in a subject, comprising:
   analyzing a sample that comprises an FGFR4 protein from the subject; and
   detecting a cysteine at an amino acid position corresponding to amino acid position 183 of the tyrosine kinase domain of the FGFR4 protein represented by SEQ ID NO: 10.

2. The method according to claim 1, wherein the detected cysteine is located at an amino acid position corresponding to amino acid position 636 in a FGFR4 protein isoform 1 represented by SEQ ID NO: 2.

3. The method according to claim 1, wherein the detected cysteine is located at an amino acid position corresponding to amino acid position 596 in a FGFR4 protein isoform 2 represented by SEQ ID NO:4.

4. A method for detecting cancer in a subject, which, comprising:
   analyzing a sample that comprises an FGFR4 protein from the subject; and
   detecting the cancer by detecting, if present, a cysteine at an amino acid position corresponding to amino acid position 183 of the tyrosine kinase domain of the FGFR4 protein represented by SEQ ID NO: 10.

5. A method for diagnosing cancer in a subject, comprising
   analyzing a sample that comprises an FGFR4 protein from the subject; and
   diagnosing the subject as having a cancer by detecting, if present, a cysteine at an amino acid position corresponding to amino acid position 183 of the tyrosine kinase domain of the FGFR4 protein represented by SEQ ID NO: 10.

* * * * *

SEQUENCE LISTING

```
<160> NUMBER OF SEQ ID NOS: 19

<210> SEQ ID NO 1
<211> LENGTH: 2409
<212> TYPE: DNA
<213> ORGANISM: Homo sapiens

<400> SEQUENCE: 1
atgcggctgc tgctggccct gttgggggtc ctgctgagtg tgcctgggcc tccagtcttg      60
tccctggagg cctctgagga agtggagctt gagccctgcc tggctcccag cctggagcag     120
caagagcagg agctgacagt agcccttggg cagcctgtgc gtctgtgctg tgggcgggct     180
gagcgtggtg gccactggta caaggagggc agtcgcctgg cacctgctgg ccgtgtacgg     240
ggctggaggg gccgcctaga gattgccagc ttcctacctg aggatgctgg ccgctacctc     300
tgcctggcac gaggctccat gatcgtcctg cagaatctca ccttgattac aggtgactcc     360
ttgacctcca gcaacgatga tgaggacccc aagtcccata gggacccctc gaataggcac     420
agttaccccc agcaagcacc ctactggaca caccccagc gcatggagaa gaaactgcat     480
gcagtacctg cggggaacac cgtcaagttc cgctgtccag ctgcaggcaa ccccacgccc     540
accatccgct ggcttaagga tggacaggcc tttcatgggg agaaccgcat tggaggcatt     600
cggctgcgcc atcagcactg gagtctcgtg atggagagcg tggtgccctc ggaccgcggc     660
acatacacct gcctggtaga gaacgctgtg ggcagcatcc gctataacta cctgctagat     720
gtgctggagc ggtccccgca ccggcccatc ctgcaggccg ggctcccggc caacaccaca     780
```

|  |  |  |  |  |  |
|---|---|---|---|---|---|
| gccgtggtgg | gcagcgacgt | ggagctgctg | tgcaaggtgt | acagcgatgc | ccagccccac | 840 |
| atccagtggc | tgaagcacat | cgtcatcaac | ggcagcagct | tcggagccga | cggtttcccc | 900 |
| tatgtgcaag | tcctaaagac | tgcagacatc | aatagctcag | aggtggaggt | cctgtacctg | 960 |
| cggaacgtgt | cagccgagga | cgcaggcgag | tacacctgcc | tcgcaggcaa | ttccatcggc | 1020 |
| ctctcctacc | agtctgcctg | gctcacggtg | ctgccagagg | aggaccccac | atggaccgca | 1080 |
| gcagcgcccg | aggccaggta | tacgacatc | atcctgtacg | cgtcgggctc | cctggccttg | 1140 |
| gctgtgctcc | tgctgctggc | cgggctgtat | cgagggcagg | cgctccacgg | ccggcacccc | 1200 |
| cgcccgcccg | ccactgtgca | gaagctctcc | cgcttccctc | tggcccgaca | gttctccctg | 1260 |
| gagtcaggct | cttccggcaa | gtcaagctca | tccctggtac | gaggcgtgcg | tctctcctcc | 1320 |
| agcggcccg | ccttgctcgc | cggcctcgtg | agtctagatc | tacctctcga | cccactatgg | 1380 |
| gagttccccc | gggacaggct | ggtgcttggg | aagcccctag | gcgagggctg | ctttggccag | 1440 |
| gtagtacgtg | cagaggcctt | tggcatggac | cctgcccggc | ctgaccaagc | cagcactgtg | 1500 |
| gccgtcaaga | tgctcaaaga | caacgcctct | gacaaggacc | tggccgacct | ggtctcggag | 1560 |
| atggaggtga | tgaagctgat | cggccgacac | aagaacatca | tcaacctgct | tggtgtctgc | 1620 |
| acccaggaag | ggcccctgta | cgtgatcgtg | gagtgcgccg | ccaagggaaa | cctgcgggag | 1680 |
| ttcctgcggg | cccggcgccc | ccaggccccc | gacctcagcc | ccgacggtcc | tcggagcagt | 1740 |
| gaggggccgc | tctccttccc | agtcctggtc | tcctgcgcct | accaggtggc | ccgaggcatg | 1800 |
| cagtatctgg | agtcccggaa | gtgtatccac | cgggacctgg | ctgcccgcaa | tgtgctggtg | 1860 |
| actgaggaca | atgtgatgaa | gattgctgac | tttgggctgg | cccgcggcgt | ccaccacatt | 1920 |
| gactactata | agaaaaccag | caacggccgc | ctgcctgtga | agtggatggc | cccgaggcc | 1980 |
| ttgtttgacc | gggtgtacac | acaccagagt | gacgtgtggt | cttttgggat | cctgctatgg | 2040 |
| gagatcttca | ccctcggggg | ctccccgtat | cctggcatcc | cggtggagga | gctgttctcg | 2100 |
| ctgctgcggg | agggacatcg | gatggaccga | ccccacact | gccccccaga | gctgtacggg | 2160 |
| ctgatgcgtg | agtgctggca | cgcagcgccc | tcccagaggc | ctaccttcaa | gcagctggtg | 2220 |
| gaggcgctgg | acaaggtcct | gctggccgtc | tctgaggagt | acctcgacct | ccgcctgacc | 2280 |
| ttcggaccct | attccccctc | tggtgggac | gccagcagca | cctgctcctc | cagcgattct | 2340 |
| gtcttcagcc | acgaccccct | gccattggga | tccagctcct | tccccttcgg | gtctggggtg | 2400 |
| cagacatga |  |  |  |  |  | 2409 |

<210> SEQ ID NO 2
<211> LENGTH: 802
<212> TYPE: PRT
<213> ORGANISM: Homo sapiens

<400> SEQUENCE: 2

Met Arg Leu Leu Leu Ala Leu Leu Gly Val Leu Leu Ser Val Pro Gly
1               5                   10                  15

Pro Pro Val Leu Ser Leu Glu Ala Ser Glu Glu Val Glu Leu Glu Pro
            20                  25                  30

Cys Leu Ala Pro Ser Leu Glu Gln Gln Glu Gln Glu Leu Thr Val Ala
        35                  40                  45

Leu Gly Gln Pro Val Arg Leu Cys Cys Gly Arg Ala Glu Arg Gly Gly
    50                  55                  60

His Trp Tyr Lys Glu Gly Ser Arg Leu Ala Pro Ala Gly Arg Val Arg
65                  70                  75                  80

-continued

```
Gly Trp Arg Gly Arg Leu Glu Ile Ala Ser Phe Leu Pro Glu Asp Ala
                85                  90                  95
Gly Arg Tyr Leu Cys Leu Ala Arg Gly Ser Met Ile Val Leu Gln Asn
            100                 105                 110
Leu Thr Leu Ile Thr Gly Asp Ser Leu Thr Ser Ser Asn Asp Asp Glu
        115                 120                 125
Asp Pro Lys Ser His Arg Asp Pro Ser Asn Arg His Ser Tyr Pro Gln
    130                 135                 140
Gln Ala Pro Tyr Trp Thr His Pro Gln Arg Met Glu Lys Lys Leu His
145                 150                 155                 160
Ala Val Pro Ala Gly Asn Thr Val Lys Phe Arg Cys Pro Ala Ala Gly
                165                 170                 175
Asn Pro Thr Pro Thr Ile Arg Trp Leu Lys Asp Gly Gln Ala Phe His
            180                 185                 190
Gly Glu Asn Arg Ile Gly Gly Ile Arg Leu Arg His Gln His Trp Ser
        195                 200                 205
Leu Val Met Glu Ser Val Val Pro Ser Asp Arg Gly Thr Tyr Thr Cys
    210                 215                 220
Leu Val Glu Asn Ala Val Gly Ser Ile Arg Tyr Asn Tyr Leu Leu Asp
225                 230                 235                 240
Val Leu Glu Arg Ser Pro His Arg Pro Ile Leu Gln Ala Gly Leu Pro
                245                 250                 255
Ala Asn Thr Thr Ala Val Val Gly Ser Asp Val Glu Leu Leu Cys Lys
            260                 265                 270
Val Tyr Ser Asp Ala Gln Pro His Ile Gln Trp Leu Lys His Ile Val
        275                 280                 285
Ile Asn Gly Ser Ser Phe Gly Ala Asp Gly Phe Pro Tyr Val Gln Val
    290                 295                 300
Leu Lys Thr Ala Asp Ile Asn Ser Ser Glu Val Glu Val Leu Tyr Leu
305                 310                 315                 320
Arg Asn Val Ser Ala Glu Asp Ala Gly Glu Tyr Thr Cys Leu Ala Gly
                325                 330                 335
Asn Ser Ile Gly Leu Ser Tyr Gln Ser Ala Trp Leu Thr Val Leu Pro
            340                 345                 350
Glu Glu Asp Pro Thr Trp Thr Ala Ala Ala Pro Glu Ala Arg Tyr Thr
        355                 360                 365
Asp Ile Ile Leu Tyr Ala Ser Gly Ser Leu Ala Leu Ala Val Leu Leu
    370                 375                 380
Leu Leu Ala Gly Leu Tyr Arg Gly Gln Ala Leu His Gly Arg His Pro
385                 390                 395                 400
Arg Pro Pro Ala Thr Val Gln Lys Leu Ser Arg Phe Pro Leu Ala Arg
                405                 410                 415
Gln Phe Ser Leu Glu Ser Gly Ser Ser Gly Lys Ser Ser Ser Ser Leu
            420                 425                 430
Val Arg Gly Val Arg Leu Ser Ser Gly Pro Ala Leu Leu Ala Gly
        435                 440                 445
Leu Val Ser Leu Asp Leu Pro Leu Asp Pro Leu Trp Glu Phe Pro Arg
    450                 455                 460
Asp Arg Leu Val Leu Gly Lys Pro Leu Gly Glu Gly Cys Phe Gly Gln
465                 470                 475                 480
Val Val Arg Ala Glu Ala Phe Gly Met Asp Pro Ala Arg Pro Asp Gln
                485                 490                 495
Ala Ser Thr Val Ala Val Lys Met Leu Lys Asp Asn Ala Ser Asp Lys
```

```
                    500                 505                 510
Asp Leu Ala Asp Leu Val Ser Glu Met Glu Val Met Lys Leu Ile Gly
        515                 520                 525

Arg His Lys Asn Ile Ile Asn Leu Leu Gly Val Cys Thr Gln Glu Gly
        530                 535                 540

Pro Leu Tyr Val Ile Val Glu Cys Ala Ala Lys Gly Asn Leu Arg Glu
545                 550                 555                 560

Phe Leu Arg Ala Arg Arg Pro Pro Gly Pro Asp Leu Ser Pro Asp Gly
                565                 570                 575

Pro Arg Ser Ser Glu Gly Pro Leu Ser Phe Pro Val Leu Val Ser Cys
            580                 585                 590

Ala Tyr Gln Val Ala Arg Gly Met Gln Tyr Leu Glu Ser Arg Lys Cys
        595                 600                 605

Ile His Arg Asp Leu Ala Ala Arg Asn Val Leu Val Thr Glu Asp Asn
        610                 615                 620

Val Met Lys Ile Ala Asp Phe Gly Leu Ala Arg Gly Val His His Ile
625                 630                 635                 640

Asp Tyr Tyr Lys Lys Thr Ser Asn Gly Arg Leu Pro Val Lys Trp Met
                645                 650                 655

Ala Pro Glu Ala Leu Phe Asp Arg Val Tyr Thr His Gln Ser Asp Val
            660                 665                 670

Trp Ser Phe Gly Ile Leu Leu Trp Glu Ile Phe Thr Leu Gly Gly Ser
        675                 680                 685

Pro Tyr Pro Gly Ile Pro Val Glu Glu Leu Phe Ser Leu Leu Arg Glu
        690                 695                 700

Gly His Arg Met Asp Arg Pro Pro His Cys Pro Pro Glu Leu Tyr Gly
705                 710                 715                 720

Leu Met Arg Glu Cys Trp His Ala Ala Pro Ser Gln Arg Pro Thr Phe
                725                 730                 735

Lys Gln Leu Val Glu Ala Leu Asp Lys Val Leu Leu Ala Val Ser Glu
            740                 745                 750

Glu Tyr Leu Asp Leu Arg Leu Thr Phe Gly Pro Tyr Ser Pro Ser Gly
        755                 760                 765

Gly Asp Ala Ser Ser Thr Cys Ser Ser Ser Asp Ser Val Phe Ser His
770                 775                 780

Asp Pro Leu Pro Leu Gly Ser Ser Ser Phe Pro Phe Gly Ser Gly Val
785                 790                 795                 800

Gln Thr

<210> SEQ ID NO 3
<211> LENGTH: 2289
<212> TYPE: DNA
<213> ORGANISM: Homo sapiens

<400> SEQUENCE: 3
atgcggctgc tgctggccct gttgggggtc ctgctgagtg tgcctggggcc tccagtcttg      60 tccctggagg cctctgagga agtggagctt gagccctgcc tggctcccag cctggagcag     120
caagagcagg agctgacagt agcccttggg cagcctgtgc gtctgtgctg tgggcgggct     180
gagcgtggtg ccactggta caaggagggc agtcgcctgg cacctgctgg ccgtgtacgg     240
ggctggaggg ccgcctaga gattgccagc ttcctacctg aggatgctgg ccgctacctc     300
tgcctggcac gaggctccat gatcgtcctg cagaatctca ccttgattac aggtgactcc     360
ttgacctcca gcaacgatga tgaggacccc aagtcccata gggacccctc gaataggcac     420
```

```
agttaccccc agcaagcacc ctactggaca cacccccagc gcatggagaa gaaactgcat    480
gcagtacctg cggggaacac cgtcaagttc cgctgtccag ctgcaggcaa ccccacgccc    540
accatccgct ggcttaagga tggacaggcc tttcatgggg agaaccgcat tggaggcatt    600
cggctgcgcc atcagcactg gagtctcgtg atggagagcg tggtgccctc ggaccgcggc    660
acatacacct gcctggtaga gaacgctgtg ggcagcatcc gctataacta cctgctagat    720
gtgctggagc ggtccccgca ccggcccatc ctgcaggccg ggctcccggc caacaccaca    780
gccgtggtgg gcagcgacgt ggagctgctg tgcaaggtgt acagcgatgc ccagccccac    840
atccagtggc tgaagcacat cgtcatcaac ggcagcagct cggagccga cggtttcccc    900 tatgtgcaag tcctaaagac tgcagacatc aatagctcag aggtggaggt cctgtacctg    960
cggaacgtgt cagccgagga cgcaggcgag tacacctgcc tcgcaggcaa ttccatcggc   1020
ctctcctacc agtctgcctg gctcacggtg ctgccaggta ctgggcgcat cccccacctc   1080
acatgtgaca gcctgactcc agcaggcaga accaagtctc ccactttgca gttctccctg   1140
gagtcaggct cttccggcaa gtcaagctca tccctggtac gaggcgtgcg tctctcctcc   1200
agcggccccg ccttgctcgc cggcctcgtg agtctctagatc tacctctcga cccactatgg   1260
gagttccccc gggacaggct ggtgcttggg aagcccctag gcgagggctg ctttggccag   1320
gtagtacgtg cagaggcctt tggcatggac cctgcccggc ctgaccaagc cagcactgtg   1380
gccgtcaaga tgctcaaaga caacgcctct gacaaggacc tggccgacct ggtctcggag   1440
atggaggtga tgaagctgat cggccgacac aagaacatca tcaacctgct tggtgtctgc   1500
acccaggaag ggcccctgta cgtgatcgtg gagtgcgccg ccaagggaaa cctgcgggag   1560
ttcctgcggg cccggcgccc cccaggcccc gacctcagcc ccgacggtcc tcggagcagt   1620 gagggggccgc tctccttccc agtcctggtc tcctgcgcct accaggtggc ccgaggcatg   1680
cagtatctgg agtcccggaa gtgtatccac cgggacctgg ctgcccgcaa tgtgctggtg   1740
actgaggaca atgtgatgaa gattgctgac tttgggctgg cccgcggcgt ccaccacatt   1800
gactactata agaaaaccag caacggccgc ctgcctgtga gtggatggc gcccgaggcc   1860 ttgtttgacc gggtgtacac acaccagagt gacgtgtggt cttttgggat cctgctatgg   1920
gagatcttca ccctcggggg ctccccgtat cctggcatcc cggtggagga gctgttctcg   1980
ctgctgcggg agggacatcg gatggaccga ccccccacact gcccccagca gctgtacggg   2040
ctgatgcgtg agtgctggca cgcagcgccc tcccagaggc ctaccttcaa gcagctggtg   2100
gaggcgctgg acaaggtcct gctggccgtc tctgaggagt acctcgacct ccgcctgacc   2160
ttcggaccct attcccctc tggtggggac gccagcagca cctgctcctc cagcgattct   2220
gtcttcagcc acgacccct gccattggga tccagctcct tccccttcgg gtctggggtg   2280
cagacatga                                                           2289
```

<210> SEQ ID NO 4
<211> LENGTH: 762
<212> TYPE: PRT
<213> ORGANISM: Homo sapiens

<400> SEQUENCE: 4

Met Arg Leu Leu Leu Ala Leu Leu Gly Val Leu Leu Ser Val Pro Gly
1               5                   10                  15

Pro Pro Val Leu Ser Leu Glu Ala Ser Glu Glu Val Glu Leu Glu Pro
            20                  25                  30

```
Cys Leu Ala Pro Ser Leu Glu Gln Gln Glu Gln Leu Thr Val Ala
            35                  40                  45

Leu Gly Gln Pro Val Arg Leu Cys Cys Gly Arg Ala Glu Arg Gly Gly
 50                  55                  60

His Trp Tyr Lys Glu Gly Ser Arg Leu Ala Pro Ala Gly Arg Val Arg
 65                  70                  75                  80

Gly Trp Arg Gly Arg Leu Glu Ile Ala Ser Phe Leu Pro Glu Asp Ala
                 85                  90                  95

Gly Arg Tyr Leu Cys Leu Ala Arg Gly Ser Met Ile Val Leu Gln Asn
            100                 105                 110

Leu Thr Leu Ile Thr Gly Asp Ser Leu Thr Ser Ser Asn Asp Asp Glu
            115                 120                 125

Asp Pro Lys Ser His Arg Asp Pro Ser Asn Arg His Ser Tyr Pro Gln
            130                 135                 140

Gln Ala Pro Tyr Trp Thr His Pro Gln Arg Met Glu Lys Lys Leu His
145                 150                 155                 160

Ala Val Pro Ala Gly Asn Thr Val Lys Phe Arg Cys Pro Ala Ala Gly
                165                 170                 175

Asn Pro Thr Pro Thr Ile Arg Trp Leu Lys Asp Gly Gln Ala Phe His
            180                 185                 190

Gly Glu Asn Arg Ile Gly Gly Ile Arg Leu Arg His Gln His Trp Ser
            195                 200                 205

Leu Val Met Glu Ser Val Val Pro Ser Asp Arg Gly Thr Tyr Thr Cys
            210                 215                 220

Leu Val Glu Asn Ala Val Gly Ser Ile Arg Tyr Asn Tyr Leu Leu Asp
225                 230                 235                 240

Val Leu Glu Arg Ser Pro His Arg Pro Ile Leu Gln Ala Gly Leu Pro
                245                 250                 255

Ala Asn Thr Thr Ala Val Val Gly Ser Asp Val Glu Leu Leu Cys Lys
            260                 265                 270

Val Tyr Ser Asp Ala Gln Pro His Ile Gln Trp Leu Lys His Ile Val
            275                 280                 285

Ile Asn Gly Ser Ser Phe Gly Ala Asp Gly Phe Pro Tyr Val Gln Val
            290                 295                 300

Leu Lys Thr Ala Asp Ile Asn Ser Ser Glu Val Glu Val Leu Tyr Leu
305                 310                 315                 320

Arg Asn Val Ser Ala Glu Asp Ala Gly Glu Tyr Thr Cys Leu Ala Gly
                325                 330                 335

Asn Ser Ile Gly Leu Ser Tyr Gln Ser Ala Trp Leu Thr Val Leu Pro
            340                 345                 350

Gly Thr Gly Arg Ile Pro His Leu Thr Cys Asp Ser Leu Thr Pro Ala
            355                 360                 365

Gly Arg Thr Lys Ser Pro Thr Leu Gln Phe Ser Leu Glu Ser Gly Ser
            370                 375                 380

Ser Gly Lys Ser Ser Ser Leu Val Arg Gly Val Arg Leu Ser Ser
385                 390                 395                 400

Ser Gly Pro Ala Leu Leu Ala Gly Leu Val Ser Leu Asp Leu Pro Leu
                405                 410                 415

Asp Pro Leu Trp Glu Phe Pro Arg Asp Arg Leu Val Leu Gly Lys Pro
            420                 425                 430

Leu Gly Glu Gly Cys Phe Gly Gln Val Val Arg Ala Glu Ala Phe Gly
            435                 440                 445

Met Asp Pro Ala Arg Pro Asp Gln Ala Ser Thr Val Ala Val Lys Met
```

```
                450             455             460
Leu Lys Asp Asn Ala Ser Asp Lys Asp Leu Ala Asp Leu Val Ser Glu
465                 470                 475                 480

Met Glu Val Met Lys Leu Ile Gly Arg His Lys Asn Ile Ile Asn Leu
                485                 490                 495

Leu Gly Val Cys Thr Gln Glu Gly Pro Leu Tyr Val Ile Val Glu Cys
                500                 505                 510

Ala Ala Lys Gly Asn Leu Arg Glu Phe Leu Arg Ala Arg Arg Pro Pro
            515                 520                 525

Gly Pro Asp Leu Ser Pro Asp Gly Pro Arg Ser Ser Glu Gly Pro Leu
            530                 535                 540

Ser Phe Pro Val Leu Val Ser Cys Ala Tyr Gln Val Ala Arg Gly Met
545                 550                 555                 560

Gln Tyr Leu Glu Ser Arg Lys Cys Ile His Arg Asp Leu Ala Ala Arg
                565                 570                 575

Asn Val Leu Val Thr Glu Asp Asn Val Met Lys Ile Ala Asp Phe Gly
                580                 585                 590

Leu Ala Arg Gly Val His His Ile Asp Tyr Tyr Lys Lys Thr Ser Asn
                595                 600                 605

Gly Arg Leu Pro Val Lys Trp Met Ala Pro Glu Ala Leu Phe Asp Arg
610                 615                 620

Val Tyr Thr His Gln Ser Asp Val Trp Ser Phe Gly Ile Leu Leu Trp
625                 630                 635                 640

Glu Ile Phe Thr Leu Gly Gly Ser Pro Tyr Pro Gly Ile Pro Val Glu
                645                 650                 655

Glu Leu Phe Ser Leu Leu Arg Glu Gly His Arg Met Asp Arg Pro Pro
                660                 665                 670

His Cys Pro Pro Glu Leu Tyr Gly Leu Met Arg Glu Cys Trp His Ala
            675                 680                 685

Ala Pro Ser Gln Arg Pro Thr Phe Lys Gln Leu Val Glu Ala Leu Asp
690                 695                 700

Lys Val Leu Leu Ala Val Ser Glu Glu Tyr Leu Asp Leu Arg Leu Thr
705                 710                 715                 720

Phe Gly Pro Tyr Ser Pro Ser Gly Gly Asp Ala Ser Ser Thr Cys Ser
                725                 730                 735

Ser Ser Asp Ser Val Phe Ser His Asp Pro Leu Pro Leu Gly Ser Ser
            740                 745                 750

Ser Phe Pro Phe Gly Ser Gly Val Gln Thr
            755                 760

<210> SEQ ID NO 5
<211> LENGTH: 2409
<212> TYPE: DNA
<213> ORGANISM: Homo sapiens

<400> SEQUENCE: 5
atgcggctgc tgctggccct gttgggggtc ctgctgagtg tgcctgggcc tccagtcttg      60
tccctggagg cctctgagga agtggagctt gagccctgcc tggctcccag cctggagcag     120
caagagcagg agctgacagt agcccttggg cagcctgtgc gtctgtgctg tgggcgggct     180
gagcgtggtg ccactggta caaggagggc agtcgcctgg cacctgctgg ccgtgtacgg     240
ggctggaggg ccgcctaga gattgccagc ttcctacctg aggatgctgg ccgctacctc     300
tgcctggcac gaggctccat gatcgtcctg cagaatctca ccttgattac aggtgactcc     360
```

```
ttgacctcca gcaacgatga tgaggacccc aagtcccata gggacccctc gaataggcac    420
agttacccccc agcaagcacc ctactggaca cacccccagc gcatggagaa gaaactgcat   480
gcagtacctg cggggaacac cgtcaagttc cgctgtccag ctgcaggcaa ccccacgccc    540
accatccgct ggcttaagga tggacaggcc tttcatgggg agaaccgcat tggaggcatt    600
cggctgcgcc atcagcactg gagtctcgtg atggagagcg tggtgccctc ggaccgcggc    660
acatacacct gcctggtaga gaacgctgtg ggcagcatcc gctataacta cctgctagat    720
gtgctggagc ggtccccgca ccggcccatc ctgcaggccg ggctcccggc caacaccaca    780
gccgtggtgg gcagcgacgt ggagctgctg tgcaaggtgt acagcgatgc ccagccccac    840
atccagtggc tgaagcacat cgtcatcaac ggcagcagct cggagccga  cggtttcccc    900
tatgtgcaag tcctaaagac tgcagacatc aatagctcag aggtggaggt cctgtacctg    960
cggaacgtgt cagccgagga cgcaggcgag tacacctgcc tcgcaggcaa ttccatcggc   1020
ctctcctacc agtctgcctg gctcacggtg ctgccagagg aggacccac atggaccgca    1080
gcagcgcccg aggccaggta tacgacatc atcctgtacg cgtcgggctc cctggccttg    1140
gctgtgctcc tgctgctggc cgggctgtat cgagggcagg cgctccacgg ccggcacccc   1200
cgcccgcccc ccactgtgca gaagctctcc cgcttccctc tggcccgaca gttctccctg   1260
gagtcaggct cttccggcaa gtcaagctca tccctggtac gaggcgtgcg tctctcctcc   1320
agcggccccg ccttgctcgc cggcctcgtg agtctagatc tacctctcga cccactatgg   1380
gagttccccc gggacaggct ggtgcttggg aagcccctag gcgagggctg ctttggccag   1440
gtagtacgtg cagaggcctt tggcatggac cctgcccggc ctgaccaagc cagcactgtg   1500
gccgtcaaga tgctcaaaga caacgcctct gacaaggacc tggccgacct ggtctcggag   1560
atggaggtga tgaagctgat cggccgacac aagaacatca tcaacctgct ggtgtctgc    1620
acccaggaag ggccctgta cgtgatcgtg gagtgcgccg ccaagggaaa cctgcgggag   1680
ttcctgcggg cccggcgccc cccaggcccc gacctcagcc ccgacggtcc tcggagcagt   1740
gaggggccgc tctccttccc agtcctggtc tcctgcgcct accaggtggc ccgaggcatg   1800
cagtatctgg agtcccggaa gtgtatccac cgggacctgg ctgcccgcaa tgtgctggtg   1860
actgaggaca atgtgatgaa gattgctgac tttgggctgg cccgctgcgt ccaccacatt   1920
gactactata agaaaaccag caacggccgc ctgcctgtga gtggatggc gcccgaggcc    1980
ttgtttgacc gggtgtacac acaccagagt gacgtgtggt cttttgggat cctgctatgg   2040
gagatcttca ccctcggggg ctccccgtat cctggcatcc cggtggagga gctgttctcg   2100
ctgctgcggg agggacatcg gatggaccga ccccccacact gcccccagaa gctgtacggg  2160
ctgatgcgtg agtgctggca cgcagcgccc tcccagaggc ctaccttcaa gcagctggtg   2220
gaggcgctgg acaaggtcct gctggccgtc tctgaggagt acctcgacct ccgcctgacc   2280
ttcggacccct attcccccctc tggtggggac gccagcagca cctgctcctc cagcgattct   2340
gtcttcagcc acgacccccct gccattggga tccagctcct tcccccttcgg gtctggggtg 2400
cagacatga                                                           2409
```

<210> SEQ ID NO 6
<211> LENGTH: 802
<212> TYPE: PRT
<213> ORGANISM: Homo sapiens

<400> SEQUENCE: 6

Met Arg Leu Leu Leu Ala Leu Leu Gly Val Leu Leu Ser Val Pro Gly

-continued

```
1               5                   10                  15
Pro Pro Val Leu Ser Leu Glu Ala Ser Glu Glu Val Glu Leu Glu Pro
                20                  25                  30
Cys Leu Ala Pro Ser Leu Glu Gln Glu Gln Glu Gln Leu Thr Val Ala
                35                  40                  45
Leu Gly Gln Pro Val Arg Leu Cys Cys Gly Arg Ala Glu Arg Gly Gly
            50                  55                  60
His Trp Tyr Lys Glu Gly Ser Arg Leu Ala Pro Ala Gly Arg Val Arg
65                  70                  75                  80
Gly Trp Arg Gly Arg Leu Glu Ile Ala Ser Phe Leu Pro Glu Asp Ala
                    85                  90                  95
Gly Arg Tyr Leu Cys Leu Ala Arg Gly Ser Met Ile Val Leu Gln Asn
                100                 105                 110
Leu Thr Leu Ile Thr Gly Asp Ser Leu Thr Ser Ser Asn Asp Asp Glu
            115                 120                 125
Asp Pro Lys Ser His Arg Asp Pro Ser Asn Arg His Ser Tyr Pro Gln
        130                 135                 140
Gln Ala Pro Tyr Trp Thr His Pro Gln Arg Met Glu Lys Lys Leu His
145                 150                 155                 160
Ala Val Pro Ala Gly Asn Thr Val Lys Phe Arg Cys Pro Ala Ala Gly
                    165                 170                 175
Asn Pro Thr Pro Thr Ile Arg Trp Leu Lys Asp Gly Gln Ala Phe His
                180                 185                 190
Gly Glu Asn Arg Ile Gly Gly Ile Arg Leu Arg His Gln His Trp Ser
            195                 200                 205
Leu Val Met Glu Ser Val Val Pro Ser Asp Arg Gly Thr Tyr Thr Cys
210                 215                 220
Leu Val Glu Asn Ala Val Gly Ser Ile Arg Tyr Asn Tyr Leu Leu Asp
225                 230                 235                 240
Val Leu Glu Arg Ser Pro His Arg Pro Ile Leu Gln Ala Gly Leu Pro
                    245                 250                 255
Ala Asn Thr Thr Ala Val Val Gly Ser Asp Val Glu Leu Leu Cys Lys
                260                 265                 270
Val Tyr Ser Asp Ala Gln Pro His Ile Gln Trp Leu Lys His Ile Val
            275                 280                 285
Ile Asn Gly Ser Ser Phe Gly Ala Asp Gly Phe Pro Tyr Val Gln Val
        290                 295                 300
Leu Lys Thr Ala Asp Ile Asn Ser Ser Glu Val Glu Val Leu Tyr Leu
305                 310                 315                 320
Arg Asn Val Ser Ala Glu Asp Ala Gly Glu Tyr Thr Cys Leu Ala Gly
                    325                 330                 335
Asn Ser Ile Gly Leu Ser Tyr Gln Ser Ala Trp Leu Thr Val Leu Pro
                340                 345                 350
Glu Glu Asp Pro Thr Trp Thr Ala Ala Ala Pro Glu Ala Arg Tyr Thr
            355                 360                 365
Asp Ile Ile Leu Tyr Ala Ser Gly Ser Leu Ala Leu Ala Val Leu Leu
        370                 375                 380
Leu Leu Ala Gly Leu Tyr Arg Gly Gln Ala Leu His Gly Arg His Pro
385                 390                 395                 400
Arg Pro Pro Ala Thr Val Gln Lys Leu Ser Arg Phe Pro Leu Ala Arg
                    405                 410                 415
Gln Phe Ser Leu Glu Ser Gly Ser Ser Gly Lys Ser Ser Ser Ser Leu
                420                 425                 430
```

Val Arg Gly Val Arg Leu Ser Ser Gly Pro Ala Leu Leu Ala Gly
        435                 440                 445

Leu Val Ser Leu Asp Leu Pro Leu Asp Pro Leu Trp Glu Phe Pro Arg
    450                 455                 460

Asp Arg Leu Val Leu Gly Lys Pro Leu Gly Glu Gly Cys Phe Gly Gln
465                 470                 475                 480

Val Val Arg Ala Glu Ala Phe Gly Met Asp Pro Ala Arg Pro Asp Gln
                485                 490                 495

Ala Ser Thr Val Ala Val Lys Met Leu Lys Asp Asn Ala Ser Asp Lys
                500                 505                 510

Asp Leu Ala Asp Leu Val Ser Glu Met Glu Val Met Lys Leu Ile Gly
            515                 520                 525

Arg His Lys Asn Ile Ile Asn Leu Leu Gly Val Cys Thr Gln Glu Gly
            530                 535                 540

Pro Leu Tyr Val Ile Val Glu Cys Ala Ala Lys Gly Asn Leu Arg Glu
545                 550                 555                 560

Phe Leu Arg Ala Arg Arg Pro Pro Gly Pro Asp Leu Ser Pro Asp Gly
                565                 570                 575

Pro Arg Ser Ser Glu Gly Pro Leu Ser Phe Pro Val Leu Val Ser Cys
            580                 585                 590

Ala Tyr Gln Val Ala Arg Gly Met Gln Tyr Leu Glu Ser Arg Lys Cys
            595                 600                 605

Ile His Arg Asp Leu Ala Ala Arg Asn Val Leu Val Thr Glu Asp Asn
        610                 615                 620

Val Met Lys Ile Ala Asp Phe Gly Leu Ala Arg Cys Val His His Ile
625                 630                 635                 640

Asp Tyr Tyr Lys Lys Thr Ser Asn Gly Arg Leu Pro Val Lys Trp Met
                645                 650                 655

Ala Pro Glu Ala Leu Phe Asp Arg Val Tyr Thr His Gln Ser Asp Val
            660                 665                 670

Trp Ser Phe Gly Ile Leu Leu Trp Glu Ile Phe Thr Leu Gly Gly Ser
            675                 680                 685

Pro Tyr Pro Gly Ile Pro Val Glu Glu Leu Phe Ser Leu Leu Arg Glu
        690                 695                 700

Gly His Arg Met Asp Arg Pro Pro His Cys Pro Pro Glu Leu Tyr Gly
705                 710                 715                 720

Leu Met Arg Glu Cys Trp His Ala Ala Pro Ser Gln Arg Pro Thr Phe
                725                 730                 735

Lys Gln Leu Val Glu Ala Leu Asp Lys Val Leu Leu Ala Val Ser Glu
            740                 745                 750

Glu Tyr Leu Asp Leu Arg Leu Thr Phe Gly Pro Tyr Ser Pro Ser Gly
            755                 760                 765

Gly Asp Ala Ser Ser Thr Cys Ser Ser Ser Asp Ser Val Phe Ser His
        770                 775                 780

Asp Pro Leu Pro Leu Gly Ser Ser Ser Phe Pro Phe Gly Ser Gly Val
785                 790                 795                 800

Gln Thr

<210> SEQ ID NO 7
<211> LENGTH: 2289
<212> TYPE: DNA
<213> ORGANISM: Homo sapiens

<400> SEQUENCE: 7

-continued

```
atgcggctgc tgctggccct gttgggggtc ctgctgagtg tgcctgggcc tccagtcttg      60
tccctggagg cctctgagga agtggagctt gagccctgcc tggctcccag cctggagcag     120
caagagcagg agctgacagt agcccttggg cagcctgtgc gtctgtgctg tgggcgggct     180
gagcgtggtg gccactggta caaggagggc agtcgcctgg cacctgctgg ccgtgtacgg     240
ggctggaggg gccgcctaga gattgccagc ttcctacctg aggatgctgg ccgctacctc     300
tgcctggcac gaggctccat gatcgtcctg cagaatctca ccttgattac aggtgactcc     360
ttgacctcca gcaacgatga tgaggacccc aagtcccata gggacccctc gaataggcac     420
agttaccccc agcaagcacc ctactggaca cacccccagc gcatggagaa gaaactgcat     480
gcagtacctg cggggaacac cgtcaagttc cgctgtccag ctgcaggcaa ccccacgccc     540
accatccgct ggcttaagga tggacaggcc tttcatgggg agaaccgcat ggaggcatt      600
cggctgcgcc atcagcactg gagtctcgtg atggagagcg tggtgccctc ggaccgcggc     660
acatacacct gcctggtaga gaacgctgtg ggcagcatcc gctataacta cctgctagat     720
gtgctggagc ggtccccgca ccggcccatc ctgcaggccg ggctcccggc caacaccaca     780
gccgtggtgg gcagcgacgt ggagctgctg tgcaaggtgt acagcgatgc ccagccccac     840
atccagtggc tgaagcacat cgtcatcaac ggcagcagct cggagccga  cggtttcccc     900
tatgtgcaag tcctaaagac tgcagacatc aatagctcag aggtgaggt  cctgtacctg     960
cggaacgtgt cagccgagga cgcaggcgag tacacctgcc tcgcaggcaa ttccatcggc    1020
ctctcctacc agtctgcctg gctcacggtg ctgccaggta ctgggcgcat ccccaccctc    1080
acatgtgaca gcctgactcc agcaggcaga accaagtctc ccactttgca gttctccctg    1140
gagtcaggct cttccggcaa gtcaagctca tccctggtac gaggcgtgcg tctctcctcc    1200
agcggccccg ccttgctcgc cggcctcgtg agtctagatc tacctctcga cccactatgg    1260
gagttccccc gggacaggct ggtgcttggg aagcccctag cgagggctg  ctttggccag    1320
gtagtacgtg cagaggcctt tggcatggac cctgcccggc ctgaccaagc cagcactgtg    1380
gccgtcaaga tgctcaaaga caacgcctct gacaaggacc tggccgacct ggtctcggag    1440
atggaggtga tgaagctgat cggccgacac aagaacatca tcaacctgct ggtgtctgc     1500
acccaggaag ggccctgta  cgtgatcgtg gagtgcgccg ccaagggaaa cctgcgggag    1560
ttcctgcggg cccggcgccc cccaggcccc gacctcagcc ccgacggtcc tcggagcagt    1620
gagggggccgc tctccttccc agtcctggtc tcctgcgcct accaggtggc ccgaggcatg    1680
cagtatctga agtcccggaa gtgtatccac cgggacctgg ctgcccgcaa tgtgctggtg    1740
actgaggaca atgtgatgaa gattgctgac tttgggctgg cccgctgcgt ccaccacatt    1800
gactactata agaaaccag  caacggccgc ctgcctgtga agtggatggc cccgaggcc     1860
tgtttgacc  gggtgtacac acaccagagt gacgtgtggt cttttgggat cctgctatgg    1920
gagatcttca ccctcggggg ctccccgtat cctggcatcc cggtgaggga gctgttctcg    1980
ctgctgcggg agggacatcg gatggaccga ccccacact  gccccccaga gctgtacggg    2040
ctgatgcgtg agtgctggca cgcagcgccc tcccagaggc ctaccttcaa gcagctggtg    2100
gaggcgctgg acaaggtcct gctggccgtc tctgaggagt acctcgacct ccgcctgacc    2160
ttcggaccct attccccctc tggtggggac gccagcagca cctgctcctc cagcgattct    2220
gtcttcagcc acgacccct  gccattggga tccagctcct tcccctt cgg gtctggggtg    2280
cagacatga                                                            2289
```

<210> SEQ ID NO 8
<211> LENGTH: 762
<212> TYPE: PRT
<213> ORGANISM: Homo sapiens

<400> SEQUENCE: 8

```
Met Arg Leu Leu Leu Ala Leu Leu Gly Val Leu Leu Ser Val Pro Gly
  1               5                  10                  15

Pro Pro Val Leu Ser Leu Glu Ala Ser Glu Glu Val Glu Leu Glu Pro
             20                  25                  30

Cys Leu Ala Pro Ser Leu Glu Gln Gln Glu Gln Glu Leu Thr Val Ala
         35                  40                  45

Leu Gly Gln Pro Val Arg Leu Cys Cys Gly Arg Ala Glu Arg Gly Gly
     50                  55                  60

His Trp Tyr Lys Glu Gly Ser Arg Leu Ala Pro Ala Gly Arg Val Arg
 65                  70                  75                  80

Gly Trp Arg Gly Arg Leu Glu Ile Ala Ser Phe Leu Pro Glu Asp Ala
                 85                  90                  95

Gly Arg Tyr Leu Cys Leu Ala Arg Gly Ser Met Ile Val Leu Gln Asn
            100                 105                 110

Leu Thr Leu Ile Thr Gly Asp Ser Leu Thr Ser Ser Asn Asp Asp Glu
        115                 120                 125

Asp Pro Lys Ser His Arg Asp Pro Ser Asn Arg His Ser Tyr Pro Gln
    130                 135                 140

Gln Ala Pro Tyr Trp Thr His Pro Gln Arg Met Glu Lys Lys Leu His
145                 150                 155                 160

Ala Val Pro Ala Gly Asn Thr Val Lys Phe Arg Cys Pro Ala Ala Gly
                165                 170                 175

Asn Pro Thr Pro Thr Ile Arg Trp Leu Lys Asp Gly Gln Ala Phe His
            180                 185                 190

Gly Glu Asn Arg Ile Gly Gly Ile Arg Leu Arg His Gln His Trp Ser
        195                 200                 205

Leu Val Met Glu Ser Val Val Pro Ser Asp Arg Gly Thr Tyr Thr Cys
    210                 215                 220

Leu Val Glu Asn Ala Val Gly Ser Ile Arg Tyr Asn Tyr Leu Leu Asp
225                 230                 235                 240

Val Leu Glu Arg Ser Pro His Arg Pro Ile Leu Gln Ala Gly Leu Pro
                245                 250                 255

Ala Asn Thr Thr Ala Val Val Gly Ser Asp Val Glu Leu Leu Cys Lys
            260                 265                 270

Val Tyr Ser Asp Ala Gln Pro His Ile Gln Trp Leu Lys His Ile Val
        275                 280                 285

Ile Asn Gly Ser Ser Phe Gly Ala Asp Gly Phe Pro Tyr Val Gln Val
    290                 295                 300

Leu Lys Thr Ala Asp Ile Asn Ser Ser Glu Val Glu Val Leu Tyr Leu
305                 310                 315                 320

Arg Asn Val Ser Ala Glu Asp Ala Gly Glu Tyr Thr Cys Leu Ala Gly
                325                 330                 335

Asn Ser Ile Gly Leu Ser Tyr Gln Ser Ala Trp Leu Thr Val Leu Pro
            340                 345                 350

Gly Thr Gly Arg Ile Pro His Leu Thr Cys Asp Ser Leu Thr Pro Ala
        355                 360                 365

Gly Arg Thr Lys Ser Pro Thr Leu Gln Phe Ser Leu Glu Ser Gly Ser
    370                 375                 380
```

```
Ser Gly Lys Ser Ser Ser Leu Val Arg Gly Val Arg Leu Ser Ser
385                 390                 395                 400

Ser Gly Pro Ala Leu Leu Ala Gly Leu Val Ser Leu Asp Leu Pro Leu
            405                 410                 415

Asp Pro Leu Trp Glu Phe Pro Arg Asp Arg Leu Val Leu Gly Lys Pro
        420                 425                 430

Leu Gly Glu Gly Cys Phe Gly Gln Val Val Arg Ala Glu Ala Phe Gly
            435                 440                 445

Met Asp Pro Ala Arg Pro Asp Gln Ala Ser Thr Val Ala Val Lys Met
450                 455                 460

Leu Lys Asp Asn Ala Ser Asp Lys Asp Leu Ala Asp Leu Val Ser Glu
465                 470                 475                 480

Met Glu Val Met Lys Leu Ile Gly Arg His Lys Asn Ile Ile Asn Leu
                485                 490                 495

Leu Gly Val Cys Thr Gln Glu Gly Pro Leu Tyr Val Ile Val Glu Cys
            500                 505                 510

Ala Ala Lys Gly Asn Leu Arg Glu Phe Leu Arg Ala Arg Arg Pro Pro
        515                 520                 525

Gly Pro Asp Leu Ser Pro Asp Gly Pro Arg Ser Ser Glu Gly Pro Leu
530                 535                 540

Ser Phe Pro Val Leu Val Ser Cys Ala Tyr Gln Val Ala Arg Gly Met
545                 550                 555                 560

Gln Tyr Leu Glu Ser Arg Lys Cys Ile His Arg Asp Leu Ala Ala Arg
                565                 570                 575

Asn Val Leu Val Thr Glu Asp Asn Val Met Lys Ile Ala Asp Phe Gly
            580                 585                 590

Leu Ala Arg Cys Val His His Ile Asp Tyr Tyr Lys Lys Thr Ser Asn
        595                 600                 605

Gly Arg Leu Pro Val Lys Trp Met Ala Pro Glu Ala Leu Phe Asp Arg
610                 615                 620

Val Tyr Thr His Gln Ser Asp Val Trp Ser Phe Gly Ile Leu Leu Trp
625                 630                 635                 640

Glu Ile Phe Thr Leu Gly Gly Ser Pro Tyr Pro Gly Ile Pro Val Glu
                645                 650                 655

Glu Leu Phe Ser Leu Leu Arg Glu Gly His Arg Met Asp Arg Pro Pro
            660                 665                 670

His Cys Pro Pro Glu Leu Tyr Gly Leu Met Arg Glu Cys Trp His Ala
        675                 680                 685

Ala Pro Ser Gln Arg Pro Thr Phe Lys Gln Leu Val Glu Ala Leu Asp
690                 695                 700

Lys Val Leu Leu Ala Val Ser Glu Glu Tyr Leu Asp Leu Arg Leu Thr
705                 710                 715                 720

Phe Gly Pro Tyr Ser Pro Ser Gly Gly Asp Ala Ser Ser Thr Cys Ser
                725                 730                 735

Ser Ser Asp Ser Val Phe Ser His Asp Pro Leu Pro Leu Gly Ser Ser
            740                 745                 750

Ser Phe Pro Phe Gly Ser Gly Val Gln Thr
        755                 760

<210> SEQ ID NO 9
<211> LENGTH: 933
<212> TYPE: DNA
<213> ORGANISM: Homo sapiens
```

```
<400> SEQUENCE: 9
ctacctctcg acccactatg ggagttcccc cgggacaggc tggtgcttgg gaagccccta    60
ggcgagggct gctttggcca ggtagtacgt gcagaggcct ttggcatgga ccctgcccgg   120
cctgaccaag ccagcactgt ggccgtcaag atgctcaaag acaacgcctc tgacaaggac   180
ctggccgacc tggtctcgga gatggaggtg atgaagctga tcggccgaca caagaacatc   240
atcaacctgc ttggtgtctg cacccaggaa gggcccctgt acgtgatcgt ggagtgcgcc   300
gccaagggaa acctgcggga gttcctgcgg gcccggcgcc cccaggccc cgacctcagc    360 cccgacggtc ctcggagcag tgaggggccg ctctccttcc cagtcctggt ctcctgcgcc   420
taccaggtgg cccgaggcat gcagtatctg agtcccgga agtgtatcca ccgggacctg    480
gctgcccgca atgtgctggt gactgaggac aatgtgatga agattgctga ctttgggctg   540
gcccgcggcg tccaccacat tgactactat aagaaaacca gcaacggccg cctgcctgtg   600
aagtggatgg cgcccgaggc cttgtttgac cgggtgtaca cacaccagag tgacgtgtgg   660
tcttttggga tcctgctatg ggagatcttc accctcgggg ctccccgta tcctggcatc    720 ccggtggagg agctgttctc gctgctgcgg gagggacatc ggatggaccg accccacac    780 tgcccccag agctgtacgg gctgatgcgt gagtgctggc acgcagcgcc ctcccagagg    840
cctaccttca gcagctggt ggaggcgctg acaaggtcc tgctggccgt ctctgaggag     900
tacctcgacc tccgcctgac cttcggaccc tat                                933

<210> SEQ ID NO 10
<211> LENGTH: 311
<212> TYPE: PRT
<213> ORGANISM: Homo sapiens

<400> SEQUENCE: 10

Leu Pro Leu Asp Pro Leu Trp Glu Phe Pro Arg Asp Arg Leu Val Leu
1               5                   10                  15

Gly Lys Pro Leu Gly Glu Gly Cys Phe Gly Gln Val Val Arg Ala Glu
            20                  25                  30

Ala Phe Gly Met Asp Pro Ala Arg Pro Asp Gln Ala Ser Thr Val Ala
        35                  40                  45

Val Lys Met Leu Lys Asp Asn Ala Ser Asp Lys Asp Leu Ala Asp Leu
    50                  55                  60

Val Ser Glu Met Glu Val Met Lys Leu Ile Gly Arg His Lys Asn Ile
65                  70                  75                  80

Ile Asn Leu Leu Gly Val Cys Thr Gln Glu Gly Pro Leu Tyr Val Ile
                85                  90                  95

Val Glu Cys Ala Ala Lys Gly Asn Leu Arg Glu Phe Leu Arg Ala Arg
            100                 105                 110

Arg Pro Pro Gly Pro Asp Leu Ser Pro Asp Gly Pro Arg Ser Ser Glu
        115                 120                 125

Gly Pro Leu Ser Phe Pro Val Leu Val Ser Cys Ala Tyr Gln Val Ala
    130                 135                 140

Arg Gly Met Gln Tyr Leu Glu Ser Arg Lys Cys Ile His Arg Asp Leu
145                 150                 155                 160

Ala Ala Arg Asn Val Leu Val Thr Glu Asp Asn Val Met Lys Ile Ala
                165                 170                 175

Asp Phe Gly Leu Ala Arg Gly Val His His Ile Asp Tyr Tyr Lys Lys
            180                 185                 190

Thr Ser Asn Gly Arg Leu Pro Val Lys Trp Met Ala Pro Glu Ala Leu
```

|     |     |     |     | 195 |     |     |     |     | 200 |     |     |     |     | 205 |
| --- | --- | --- | --- | --- | --- | --- | --- | --- | --- | --- | --- | --- | --- | --- |

Phe Asp Arg Val Tyr Thr His Gln Ser Asp Val Trp Ser Phe Gly Ile
210                     215                     220

Leu Leu Trp Glu Ile Phe Thr Leu Gly Gly Ser Pro Tyr Pro Gly Ile
225                     230                     235                 240

Pro Val Glu Glu Leu Phe Ser Leu Leu Arg Gly His Arg Met Asp
                    245                     250                     255

Arg Pro Pro His Cys Pro Pro Glu Leu Tyr Gly Leu Met Arg Glu Cys
                260                     265                     270

Trp His Ala Ala Pro Ser Gln Arg Pro Thr Phe Lys Gln Leu Val Glu
                275                     280                     285

Ala Leu Asp Lys Val Leu Leu Ala Val Ser Glu Glu Tyr Leu Asp Leu
                290                     295                     300

Arg Leu Thr Phe Gly Pro Tyr
305                     310

<210> SEQ ID NO 11
<211> LENGTH: 20
<212> TYPE: DNA
<213> ORGANISM: Homo sapiens

<400> SEQUENCE: 11
cactgtggcc gtcaagatgc                                          20

<210> SEQ ID NO 12
<211> LENGTH: 24
<212> TYPE: DNA
<213> ORGANISM: Homo sapiens

<400> SEQUENCE: 12
tgctggtttt cttatagtag tcaa                                     24

<210> SEQ ID NO 13
<211> LENGTH: 24
<212> TYPE: DNA
<213> ORGANISM: Homo sapiens

<400> SEQUENCE: 13
atgctcaaag acaacgcctc tgac                                     24

<210> SEQ ID NO 14
<211> LENGTH: 35
<212> TYPE: DNA
<213> ORGANISM: Artificial Sequence
<220> FEATURE:
<223> OTHER INFORMATION: primer for cloning

<400> SEQUENCE: 14
gccactagta tgcggctgct gctggccctg ttggg                         35

<210> SEQ ID NO 15
<211> LENGTH: 34
<212> TYPE: DNA
<213> ORGANISM: Artificial Sequence
<220> FEATURE:
<223> OTHER INFORMATION: primer for cloning

<400> SEQUENCE: 15
gccgtcgact catgtctgca ccccagaccc gaag                          34

<210> SEQ ID NO 16

```
<211> LENGTH: 27
<212> TYPE: DNA
<213> ORGANISM: Homo sapiens

<400> SEQUENCE: 16
ggcccgctgc gtccaccaca ttgacta                                          27

<210> SEQ ID NO 17
<211> LENGTH: 27
<212> TYPE: DNA
<213> ORGANISM: Homo sapiens

<400> SEQUENCE: 17
tggacgcagc gggccagccc aaagtca                                          27

<210> SEQ ID NO 18
<211> LENGTH: 30
<212> TYPE: DNA
<213> ORGANISM: Artificial Sequence
<220> FEATURE:
<223> OTHER INFORMATION: primer for cloning

<400> SEQUENCE: 18
tggaattctg cagatatgcg gctgctgctg                                       30

<210> SEQ ID NO 19
<211> LENGTH: 30
<212> TYPE: DNA
<213> ORGANISM: Artificial Sequence
<220> FEATURE:
<223> OTHER INFORMATION: primer for cloning

<400> SEQUENCE: 19
cggtgacacg acctatcatg tctgcacccc                                       30
```